United States Patent
Hert et al.

(10) Patent No.: US 10,882,857 B2
(45) Date of Patent: Jan. 5, 2021

(54) BICYCLIC COMPOUNDS AS ATX INHIBITORS

(71) Applicant: Hoffmann-La Roche Inc., Little Falls, NJ (US)

(72) Inventors: Jérôme Hert, Basel (CH); Daniel Hunziker, Basel (CH); Patrizio Mattei, Basel (CH); Markus Rudolph, Basel (CH); Petra Schmitz, Basel (CH); Patrick Di Giorgio, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/569,459

(22) Filed: Sep. 12, 2019

(65) Prior Publication Data

US 2020/0002336 A1   Jan. 2, 2020

Related U.S. Application Data

(63) Continuation of application No. PCT/EP2018/056324, filed on Mar. 14, 2018.

(30) Foreign Application Priority Data

Mar. 16, 2017 (EP) .................................... 17161254

(51) Int. Cl.
| | |
|---|---|
| C07D 471/04 | (2006.01) |
| C07D 405/14 | (2006.01) |
| A61K 9/20 | (2006.01) |
| A61K 9/48 | (2006.01) |
| C07D 498/04 | (2006.01) |
| C07D 401/14 | (2006.01) |
| C07D 495/04 | (2006.01) |
| C07D 513/04 | (2006.01) |
| C07D 519/00 | (2006.01) |

(52) U.S. Cl.
CPC .......... *C07D 471/04* (2013.01); *A61K 9/2009* (2013.01); *A61K 9/2054* (2013.01); *A61K 9/2059* (2013.01); *A61K 9/2095* (2013.01); *A61K 9/485* (2013.01); *A61K 9/4858* (2013.01); *A61K 9/4866* (2013.01); *C07D 401/14* (2013.01); *C07D 405/14* (2013.01); *C07D 495/04* (2013.01); *C07D 498/04* (2013.01); *C07D 513/04* (2013.01); *C07D 519/00* (2013.01)

(58) Field of Classification Search
CPC .. C07D 471/04; C07D 405/14; C07D 498/04; C07D 401/14; C07D 519/00; C07D 513/04; C07D 495/04; A61K 9/20; A61K 9/48
USPC ......................................................... 514/302
See application file for complete search history.

(56) References Cited

U.S. PATENT DOCUMENTS

| | | |
|---|---|---|
| 3,392,149 A | 7/1968 | von der Emden et al. |
| 5,202,322 A | 4/1993 | Allen et al. |
| 5,238,942 A | 8/1993 | Chakravarty et al. |
| 5,240,928 A | 8/1993 | Allen et al. |
| 5,290,780 A | 3/1994 | Venkatesan et al. |
| 5,304,565 A | 4/1994 | Morimoto et al. |
| 5,358,951 A | 10/1994 | Levin et al. |
| 5,470,975 A | 11/1995 | Atwal et al. |
| 5,472,961 A | 12/1995 | Gottschlich et al. |
| 5,532,243 A | 7/1996 | Gilligan |
| 6,821,964 B2 | 11/2004 | Colon-Cruz et al. |
| 6,841,560 B2 | 1/2005 | Thompson et al. |
| 7,271,260 B2 | 9/2007 | Lee et al. |
| 8,329,907 B2 | 12/2012 | Schultz et al. |
| 8,440,694 B2 | 5/2013 | Turner et al. |
| 8,697,883 B2 | 4/2014 | Abouabdellah et al. |
| 8,841,324 B2 | 9/2014 | Staehle et al. |
| 8,946,264 B2 | 2/2015 | Shinozuka et al. |

(Continued)

FOREIGN PATENT DOCUMENTS

| | | |
|---|---|---|
| CA | 2768095 | 1/2011 |
| CA | 2878442 A1 | 4/2014 |

(Continued)

OTHER PUBLICATIONS 959567-58-9,CAS Database Registry [retrieved online May 25, 2016] Chemical Abstracts Service Dec. 26, 2007 (Dec. 26, 2007), NIH Chemical Genomics Center:, retrieved from STN Database accession No. 959567-58-9.

(Continued)

*Primary Examiner* — Niloofar Rahmani
(74) *Attorney, Agent, or Firm* — Katherine J. Mackenzie

(57) ABSTRACT

The invention provides novel compounds having the general formula (I)

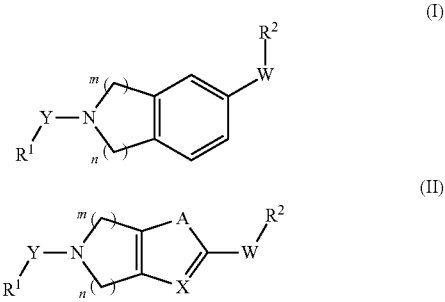

wherein $R^1$, $R^2$, Y, W, A, X, m and n are as defined herein, compositions including the compounds and methods of using the compounds.

30 Claims, No Drawings

(56) References Cited

U.S. PATENT DOCUMENTS

| | | |
|---|---|---|
| 9,029,387 B2 | 5/2015 | Staehle et al. |
| 9,493,486 B2 | 11/2016 | Hunziker et al. |
| 9,580,434 B2 | 2/2017 | Mazurov et al. |
| 9,598,418 B2 | 3/2017 | Srivastava et al. |
| 9,802,944 B2 | 10/2017 | Di Giorgio et al. |
| 10,208,052 B1 | 2/2019 | Zheng et al. |
| 10,633,384 B2 | 4/2020 | Hunziker et al. |
| 10,640,472 B2 | 5/2020 | Hert et al. |
| 10,647,719 B2 | 5/2020 | Di Giorgio et al. |
| 10,654,857 B2 | 5/2020 | Di Giorgio et al. |
| 10,669,268 B2 | 6/2020 | Hert et al. |
| 10,669,285 B2 | 6/2020 | Hunziker et al. |
| 10,676,446 B2 | 6/2020 | Hert et al. |
| 2005/0203112 A1 | 9/2005 | Castonguay et al. |
| 2008/0090802 A1 | 4/2008 | Letourneau et al. |
| 2010/0222341 A1 | 9/2010 | Schiemann et al. |
| 2010/0298290 A1 | 11/2010 | Kumar et al. |
| 2011/0230471 A1 | 9/2011 | Staehle et al. |
| 2012/0015959 A1 | 1/2012 | Staehle et al. |
| 2012/0095040 A1 | 4/2012 | Abouabdellah et al. |
| 2012/0115852 A1 | 5/2012 | Schultz et al. |
| 2012/0115858 A1 | 5/2012 | Tesconi et al. |
| 2015/0252046 A1 | 9/2015 | Staehle et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |
| 2017/0029425 A1 | 2/2017 | Hunziker et al. |
| 2017/0050960 A1 | 2/2017 | Hert et al. |
| 2018/0118741 A1 | 5/2018 | Hert et al. |
| 2018/0208601 A1 | 7/2018 | Hert et al. |
| 2018/0208602 A1 | 7/2018 | Di Giorgio et al. |
| 2018/0215765 A1 | 8/2018 | Di Giorgio et al. |
| 2018/0258095 A1 | 9/2018 | Hert et al. |
| 2018/0280352 A1 | 10/2018 | Mattei et al. |
| 2018/0312515 A1 | 11/2018 | Mattei et al. |
| 2018/0327410 A1 | 11/2018 | Grice et al. |
| 2018/0327416 A1 | 11/2018 | Grice et al. |
| 2019/0144457 A1 | 5/2019 | Di Giorgio et al. |
| 2020/0002297 A1 | 1/2020 | Mattei et al. |
| 2020/0002336 A1 | 1/2020 | Hert et al. |
| 2020/0079779 A1 | 3/2020 | Di Giorgio et al. |
| 2020/0087307 A1 | 3/2020 | Mattei et al. |
| 2020/0199155 A1 | 6/2020 | Hunziker et al. |
| 2020/0207769 A1 | 7/2020 | Hunziker et al. |
| 2020/0216457 A1 | 7/2020 | Di Giorgio et al. |

FOREIGN PATENT DOCUMENTS

| | | |
|---|---|---|
| CN | 1068114 A | 1/1993 |
| CN | 1751047 A1 | 3/2006 |
| CN | 102459207 A | 5/2012 |
| CN | 103237799 A | 8/2013 |
| CN | 104428299 A | 3/2015 |
| CN | 104918917 A | 9/2015 |
| EP | 0417631 A2 | 3/1991 |
| EP | 0 424 850 A1 | 5/1991 |
| EP | 2301936 A1 | 3/2011 |
| EP | 3 187 492 A1 | 7/2017 |
| EP | 3385261 A1 | 10/2018 |
| JP | 2001-039950 | 2/2001 |
| JP | 2005-239708 | 9/2005 |
| JP | 2007-176809 | 7/2007 |
| JP | 2008-501743 | 1/2008 |
| JP | 2008-31064 | 2/2008 |
| JP | 2008-031064 A | 2/2008 |
| JP | 2008-513533 | 8/2008 |
| JP | 2008-540547 | 11/2008 |
| JP | 2009-161449 | 7/2009 |
| JP | 2011-502150 | 1/2011 |
| KR | 2006-0088557 | 8/2006 |
| RU | 2375352 C2 | 12/2009 |
| RU | 2 480 463 | 4/2013 |
| RU | 2 483 068 | 5/2013 |
| RU | 2 517 693 | 5/2014 |
| WO | 99/40070 | 8/1999 |
| WO | 01/30780 | 5/2001 |
| WO | 02/070523 A1 | 9/2002 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/090143 | 8/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008/135141 A1 | 11/2008 |
| WO | 2009/046841 A2 | 4/2009 |
| WO | 2009/054914 A1 | 4/2009 |
| WO | 2009/058347 | 5/2009 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108268 | 9/2010 |
| WO | 2010/108651 | 9/2010 |
| WO | 2010/112116 A1 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/144817 A1 | 12/2010 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A1 | 11/2011 |
| WO | 2009/154132 | 12/2011 |
| WO | 2011/151461 A2 | 12/2011 |
| WO | 2012/020008 A1 | 2/2012 |
| WO | 2012/024620 | 2/2012 |
| WO | 2012/028243 | 3/2012 |
| WO | 2012/080727 A1 | 6/2012 |
| WO | 2012/166415 A1 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 A1 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014179564 * | 6/2014 |
| WO | 2014/102817 A1 | 7/2014 |
| WO | 2014/133112 A1 | 9/2014 |
| WO | 2014/139324 | 9/2014 |
| WO | 2014/139978 A1 | 9/2014 |

(56) References Cited

FOREIGN PATENT DOCUMENTS

| | | |
|---|---|---|
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/077503 A1 | 5/2015 |
| WO | 2015/078800 A1 | 6/2015 |
| WO | 2015/078803 | 6/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/154023 A1 | 10/2015 |
| WO | 2016/031987 | 3/2016 |
| WO | 2016/061160 A1 | 4/2016 |
| WO | 2016/128529 A1 | 8/2016 |
| WO | 2016/162390 | 10/2016 |
| WO | 2017/005073 A1 | 1/2017 |
| WO | 2017/037146 | 3/2017 |
| WO | 2017/037670 A1 | 3/2017 |
| WO | 2017/050732 A1 | 3/2017 |
| WO | 2017/050747 A1 | 3/2017 |
| WO | 2017/050791 A1 | 3/2017 |
| WO | 2017/050792 A1 | 3/2017 |
| WO | 2017/053722 A1 | 3/2017 |
| WO | 2017/091673 A2 | 6/2017 |
| WO | 2018/167001 A1 | 9/2018 |
| WO | 2018/167113 A1 | 9/2018 |

OTHER PUBLICATIONS

Albers et al., "Chemical Evolution of Autotaxin Inhibitors" Chemical Reviews (XP055073234), 112(5):2593-2603 (May 9, 2012).

Albers et al., "Structure-Based Design of Novel Boronic Acid-Based Inhibitors of Autotaxin" Journal of Medicinal Chemistry 54(13):4619-4626 ( 2011).

Albers, H., et al., "Discovery and Optimization of Boronic Acid Based Inhibitors of Autotaxin" J Med Chem 53:4958-4967 (Jun. 10, 2010).

Anderson, "The Process of Structure-Based Drug Design" Chemistry & Biology 10:787-797 (Sep. 2003).

Angeli et al., "Synthesis and carbonic anhydrase inhibition of polycyclic imides moieties" Bioorgan Med Chem 25(20):5373-5379 (Oct. 20, 2017).

Armstrong, J., et al., "Purification and Properties of Human Erythrocyte Carbonic Anhydrases" J Biol Chem 241(21):5137-5149 (Nov. 10, 1966).

Barbayianni Efrosini, "Autotaxin inhibitors:a patent review" Expert Opin Ther Pat 23(9):1123-1132 (Sep. 1, 2013).

Benesch, Matthew G.K., et al., "Autotaxin in the crosshairs: Taking aim at cancer and other inflammatory conditions" FEBS LETT 588:2712-2727 (Feb. 19, 2014).

Bora, Rajesh O., et al., "[1, 2, 4]-Oxadiazoles: Synthesis and Biological Applications" Mini-Reviews in Med. Chem 14(4):355-369 (Mar. 13, 2014).

CAS Database Registry, ID#1206969-43-8 [retrieved online May 25, 2016], Feb. 22, 2010 (Feb. 22, 2010), BroadPharm:, retrieved from STN Database accession No. 1206969-43-8 the whole document.

CAS Registry Database, 1300725-30-7,Database Registry [retrieved online May 25, 2016] Chemical Abstracts Service May 25, 2011 (May 25, 2011), Focus Synthesis LLC:, retrieved from STN Database accession No. 1300725-30-7 the whole document.

Database Capulus (online) Chemical Abstracts Service Columbus Ohio, 1993, Database accession No. 1994:483155 RN156411-73-3, 156411-74-4 (1993).

Erdik, Ender, "Transition Metal Catalyzed Reactions of Organozinc Reagents" Tetrahedron Rep No. 23 48(44):9577-9648 (Jan. 1, 1992).

Farina, V. et al. Organic Reactions "The Stille Reaction" Paquette, Leo A., New York-US:Wiley and Sons, vol. 50:1-704 (Apr. 1, 1997).

Garcia-Gutierrez et al., "Novel inhibitors to Taenia solium Cu/Zn superoxide dismutase identifed by virtual screening" J. Comp Aided Molecular Design 25:1135-1145 (2011).

Gierse et al., "A Novel Autotaxin Inhibitor Reduces Lysophosphatidic Acid Levels in Plasma and the Site of Inflammation" Pharmacol Exp Ther 334:310-317 ( 2010).

Green et al. Protective Groups in Organic Synthesis (Table of Contents only, in 4 pages), Second edition, New York: John Wiley & Sons, Inc., ( 1991).

Hall, Dennis, ed. et al. Boronic Acids: Preparation, Applications in Organic Synthesis and Medicine (Description and table of contents only, 2 pages), Hall, Dennis,Wiley,:1-571 (Jan. 1, 2006).

Hemming, K. Science of Synthesis, Product 13: 1, 2, 3-Triazoles "Product Class 6: 1,2,4-Oxadiazoles" Storr, R.C. & Gilchrist, T.L., eds., Stuttgart-DE: Thieme Verlagsgruppe, vol. 13:127-184 (Jan. 1, 2004).

Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).

Hoeglund et al., "Optimization of a pidemidic acid autotaxin inhibitor" J Med Chem 53:1056-1066 (Dec. 30, 2009).

"International Preliminary Report on Patentability—PCT/EP2018/056140":pp. 1-8 (dated Sep. 26, 2019).

"International Search Report—PCT/EP2014/054631":pp. 1-4 (dated Apr. 15, 2014).

"International Search Report—PCT/EP2014/075360":pp. 1-5 (dated Feb. 9, 2015).

"International Search Report—PCT/EP2015/056041":pp. 1-5 (dated May 6, 2015).

"International Search Report—PCT/EP2016/072277":pp. 1-5 (dated Dec. 8, 2016).

"International Search Report—PCT/EP2016/072349":pp. 1-5 (dated Nov. 29, 2016).

"International Search Report—PCT/EP2018/056140":pp. 1-9 (dated May 4, 2018).

"International Search Report—PCT/EP2018/056324",:pp. 1-7 (dated May 8, 2018).

"International Search Report—PCT/EP2013/061890",:pp. 1-9 (dated Sep. 17, 2013).

"International Search Report—PCT/EP2013/069679":pp. 1-3 (dated Nov. 8, 2013).

"International Search Report—PCT/EP2015/056032",:pp. 1-5 (dated Apr. 23, 2015).

"International Search Report—PCT/EP2016/057549":pp. 1-5 (dated Jun. 22, 2016).

"International Search Report—PCT/EP2016/072243":pp. 1-5 (dated Dec. 6, 2016).

"International Search Report—PCT/EP2016/072347":pp. 1-5 (dated Jan. 17, 2017).

"International Search Report—PCT/EP2016/070561":pp. 1-6 (dated Oct. 28, 2016).

Jones et al., "Novel autotaxin inhibitors for the treatment of osteoarthritis pain: Lead optimization via structure based drug design" ACS Med Chem Lett 7(9):857-861 (Sep. 8, 2016).

Kung et al., "Identification of spirocyclic piperidine-azetidine inverse agonists of the ghrelin receptor" Bioorg Med Chem Lett, 22(13):4281-4287 (May 8, 2012).

Li, Jie Jack et al. Name Reactions for Homologation, Part 1 "Name Reactions for Homologation, Part 1" (Abstract of text, author information, and table of contents only, 2 pages),Wiley and Sons,:1-685 (May 1, 2009).

Litherland et al., "The Amino-derivatives of Pentuerythritol. Part I. Preparation." J Chem Soc:1588-1595 (Jan. 1, 1938).

Matralis et al., "Development and therapeutic potential of autotaxin small molecule inhibitors: From bench to advanced clinical trials" Med. Res. Rev.:1-38 ( 2018).

Mayo Clinic Staff, (Lupus [online], retrieved from the internet on Jan. 24, 2017; http://www.mayoclinic.org/diseases-conditions/lupus basics/definition/CON-20019676) 2017.

(56) References Cited

OTHER PUBLICATIONS

Mitchell, Terence N., "Palladium-Catalysed Reactions of Organotin Compounds" Synthesis 9:803-815 (Aug. 16, 1991).
Negishi, et al. Metal-Catalyzed Cross-Coupling Reactions "Chapter 1: Palladium or NickelCatalyzed Cross Coupling with Organometals Containing Zinc, Magnesium, Aluminum, and Zirconium" (Preface, table of contents, list of contributors only, 22 pages), Diederich, Francois, Stang, Peter J., eds., Weinheim, DE:Wiley-VCH Verlag GmbH,:1-47 (Jan. 1, 2004).
Orr et al., "One-pot synthesis of chiral azetidines from chloroaldehyde and chiral amines" Tetrahedron Lett 52:36183620 (May 14, 2011).
Overberger et al., "Absolute Configuration of 2,7-Diazaspiro[4.4]nonane. A Reassignment" J. Org. Chem. 46(13):2757-2764 (Jun. 1, 1981).
Patani, G., et al., "Bioisosterism: A Rational Approach in Drug Design" Chem Rev 96(8):3147-3176 (Dec. 19, 1996).
Polshettiwar, V., et al., "Suzuki-Miyaura Cross-Coupling Reactions in Aqueous Media: Green and Sustainable Syntheses of Biaryls" Chem Sus Chem 3:502-522 (Jan. 1, 2010).
Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993 (Oct. 27, 2012)
Schlaeger, E. et al., "The protein hydrolysate, primatone RL, is a cost-effective multiple growth promoter of mammalian cel culture in serum-containing and serum-free medi and displays anti-apoptosis properties" J Immunol Methods 194:191-199 (Apr. 12, 1996).
Sheridan et al., "Cautious optimism surrounds early clinical data for PD-1 blocker" Nat Biotechnol 30(8):729-730 (Aug. 1, 2012).
Sheridan et al., "The Most Common Chemical Replacements in Drug-Like Compounds" J. Chem. Inf. Comput. Sci. 42(1):103-108 ( 2002).
Sippy et al., "Preparation and characterization of N-(3-pyridinyl) spirocyclic diamines as ligands for nicotinic acetylcholine receptors" Bioorg Med Chem Lett 19:1682-1685 (Feb. 4, 2009).
Stille, John K., "The Palladium-Catalyzed Cross-Coupling Reactions of Organotin Reagents with Organic Electrophiles" Angew Chem. Int. Ed. Engl. 25:508-524 (Jan. 1, 1986).
STN Columbus (STN International), pp. 1-13 ( Oct. 9, 2015).
Stocks et al., "A Practical Method for Targeted Library Design Balancing Lead-like Properties with Diversity" Chem Med Chem, 4:800-808 ( 2009).
Suzuki, A., et al., "Palladium-Catalyzed Cross-Coupling Reactions of Organoboron Compounds" Chem Rev. 95:2457-2483 (Jan. 31, 1995).
Suzuki, A., et al., "Recent advances in the cross-coupling reactions of organoboron derivatives with organic electrophiles, 1995-1998" J Organomet Chem 576:147-168 (Jan. 1, 1999).
Suzuki, A., et al., "Synthetic Studies via the cross-coupling reaction of organoboron derivatives with organic halides" Pure Appl Chem 63(3):419-422 (Jan. 1, 1991).
Thiel,, "Structure-aided drug design's next generation" Nat Biotechnol 22(5):513-519 (May 1, 2004).
Tucker, T., et al., "Discovery of 3-{5-[(6-Amino-1H-pyrazolo[3,4-b]pyridine-3-yl)methoxy]-2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J Med Chem 51:6503-6511 (Jul. 11, 2008).
CAS Registry Database, 1352926-14-7,Database Registry [retrieved online May 25, 2016] Chemical Abstracts Service Jan. 12, 2012 (Jan. 12, 2012), All i chern LLC: XP002707617, retrieved from STN Database accession No. 1352926-14-7 see also RN: 135295-74-6; the whole document.
CAS Registry Database, 959567-58-9, pp. 1-38 Dec. 26, 2007.
Liu, Medicinal Chemistry (English translation),:349 (Aug. 31, 2007).
Tan, Pharmacology (English translation),:27-28 (Jul. 31, 2006).
"U.S. Appl. No. 16/793,178, filed Feb. 18, 2020".
"U.S. Appl. No. 16/811,656, filed Mar. 6, 2020".
"U.S. Appl. No. 16/818,409, filed Mar. 13, 2020".
"U.S. Appl. No. 16/832,553, filed Mar. 27, 2020".
"U.S. Appl. No. 16/889,322, filed Jun. 1, 2020".
Written Opinion for PCT/EP2013/061890.
Written Opinion for PCT/EP2013/069679.

* cited by examiner

BICYCLIC COMPOUNDS AS ATX INHIBITORS

This application is a continuation of International Application No. PCT/EP2018/056324, filed Mar. 14, 2018, which claims priority to EP Application No. 17161254.2 filed Mar. 16, 2017, each of which is incorporated herein by reference in its entirety.

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I) or (II)

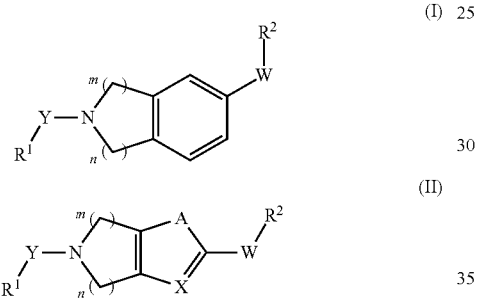

wherein
$R^1$ is selected from the groups consisting of
i) phenyl substituted by $R^3$, $R^4$ and $R^5$,
ii) phenyl-$C_{1-6}$-alkyl substituted by $R^3$, $R^4$ and $R^5$,
iii) phenoxy-$C_{1-6}$-alkyl substituted by $R^3$, $R^4$ and $R^5$,
iv) phenyl-$C_{2-6}$-alkenyl substituted by $R^3$, $R^4$ and $R^5$,
v) phenyl-$C_{2-6}$-alkynyl substituted by $R^3$, $R^4$ and $R^5$,
vi) pyridinyl substituted by $R^3$, $R^4$ and $R^5$,
vii) pyridinyl-$C_{1-6}$-alkyl substituted by $R^3$, $R^4$ and $R^5$,
viii) pyridinyl-$C_{2-6}$-alkenyl substituted by $R^3$, $R^4$ and $R^5$,
ix) pyridinyl-$C_{2-6}$-alkynyl substituted by $R^3$, $R^4$ and $R^5$,
x) thiophenyl substituted by $R^3$, $R^4$ and $R^5$,
xi) thiophenyl-$C_{1-6}$-alkyl substituted by $R^3$, $R^4$ and $R^5$,
xii) thiophenyl-$C_{2-6}$-alkenyl substituted by $R^3$, $R^4$ and $R^5$, and
xiii) thiophenyl-$C_{2-6}$-alkynyl substituted by $R^3$, $R^4$ and $R^5$;
Y is selected from the groups consisting of
i) —OC(O)—, and
ii) —C(O)—;
A is selected from the groups consisting of
i) —O—, and
ii) —S—;
X is selected from the groups consisting of
i) —N—, and
ii) —CH—;
W is selected from the groups consisting of
i) —C(O)—, and
ii) —S(O)$_2$—;

$R^2$ is selected from the ring systems O, AO, AW, AX, AY and AZ;

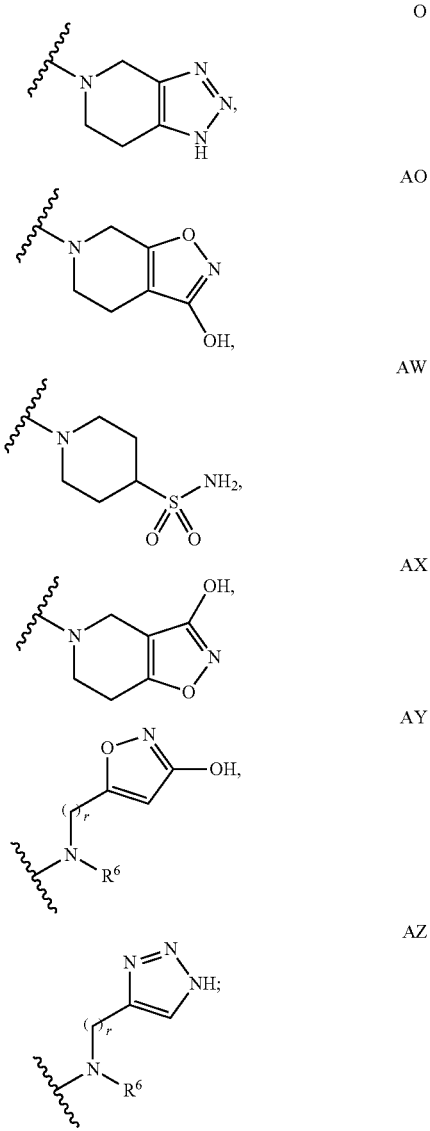

$R^3$ is selected from the groups consisting of
i) halogen,
ii) hydroxy,
iii) cyano, $C_{1-6}$-alkyl,
iv) $C_{1-6}$-alkoxy,
v) $C_{1-6}$-alkoxy-$C_{1-6}$-alkyl,
vi) halo-$C_{1-6}$-alkoxy,
vii)
viii) hydroxy-$C_{1-6}$-alkyl,
ix) $C_{3-8}$-cycloalkyl,
x) $C_{3-8}$-cycloalkyl-$C_{1-6}$-alkyl,
xi) $C_{3-8}$-cycloalkyl-$C_{1-6}$-alkoxy,
xii) $C_{3-8}$-cycloalkoxy,
xiii) $C_{3-8}$-cycloalkoxy-$C_{1-6}$-alkyl,
xiv) $C_{1-6}$-alkylamino,
xv) $C_{1-6}$-alkylcarbonylamino,
xvi) $C_{3-8}$-cycloalkylcarbonylamino,
xvii) $C_{1-6}$-alkyltetrazolyl, xviii) $C_{1-6}$-alkyltetrazolyl-$C_{1-6}$-alkyl, and
xix) heterocycloalkyl-$C_{1-6}$-alkoxy;
$R^4$ and $R^5$ are independently selected from the groups consisting of
  i) H,
  ii) halogen,
  iii) hydroxy,
  iv) cyano,
  v) $C_{1-6}$-alkyl,
  vi) $C_{1-6}$-alkoxy,
  vii) $C_{1-6}$-alkoxy-$C_{1-6}$-alkyl,
  viii) halo-$C_{1-6}$-alkoxy,
  ix) halo-$C_{1-6}$-alkyl,
  x) hydroxy-$C_{1-6}$-alkyl,
  xi) $C_{3-8}$-cycloalkyl,
  xii) $C_{3-8}$-cycloalkyl-$C_{1-6}$-alkyl,
  xiii) $C_{3-8}$-cycloalkyl-$C_{1-6}$-alkoxy,
  xiv) $C_{3-8}$-cycloalkoxy,
  xv) $C_{3-8}$-cycloalkoxy-$C_{1-6}$-alkyl,
  xvi) $C_{1-6}$-alkylcarbonylamino,
  xvii) $C_{3-8}$-cycloalkylcarbonylamino,
  xviii) $C_{1-6}$-alkyltetrazolyl,
  xix) $C_{1-6}$-alkyltetrazolyl-$C_{1-6}$-alkyl, and
  xx) heterocycloalkyl-$C_{1-6}$-alkoxy;
$R^6$ is selected from the groups consisting of
  i) H,
  ii) $C_{1-6}$-alkyl, and
  iii) $C_{3-8}$-cycloalkyl;
  m and n are independently selected from 1, 2 and 3;
  r is 1, 2 or 3;
or pharmaceutically acceptable salts.

Autotaxin (ATX) is a secreted enzyme also called ectonucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2NZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective puringeric receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and-chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particulary, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

The term "$C_2$-$C_6$-alkenyl" denotes a monovalent linear or branched hydrocarbon group of 2 to 6 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "$C_1$-$C_6$-alkoxy" denotes a group of the formula —O—R', wherein R' is a $C_1$-$C_6$-alkyl group. Examples of $C_1$-$C_6$-alkoxy group include methoxy, ethoxy, n-propoxy, isopropoxy, n-butoxy, isobutoxy and tert-butoxy.

The term "$C_1$-$C_6$-alkoxy-$C_{1-6}$-alkyl" denotes a $C_1$-$C_6$-alkyl group wherein at least one of the hydrogen atoms of the $C_1$-$C_6$-alkyl group is replaced by a $C_1$-$C_6$-alkoxy group. Particular examples are methoxymethyl, methoxyethyl, ethoxymethyl, ethoxyethyl, iso-propoxymethyl and iso-propoxyethyl.

The term "$C_1$-$C_6$-alkyl" denotes a monovalent linear or branched saturated hydrocarbon group of 1 to 6 carbon atoms. Examples of $C_1$-$C_6$-alkyl include methyl, ethyl, propyl, isopropyl, n-butyl, iso-butyl, sec-butyl, tert-butyl and pentyl. Particular alkyl groups include methyl, isopropyl and tert-butyl.

The term "$C_1$-$C_6$-alkylamino" denotes an amino group wherein the nitrogen atom is substituted by one H atom and one $C_1$-$C_6$-alkyl group. Examples are group wherein the $C_1$-$C_6$-alkyl group is selected from methyl, ethyl, propyl, isopropyl, n-nutyl, sec-butyl and tert-butyl.

The term "$C_1$-$C_6$-alkylcarbonyl" denotes a group of the formula —C(O)—R', wherein R' is a $C_1$-$C_6$-alkyl group. Examples of $C_1$-$C_6$-alkylcarbonyl group include groups wherein R' is methoxy, ethoxy, n-propoxy, isopropoxy, n-butoxy, isobutoxy and tert-butoxy.

The term "$C_1$-$C_6$-alkylcarbonylamino" denotes an amino group wherein the nitrogen atom is substituted by one H atom and by a $C_1$-$C_6$-alkylcarbonyl group. Particular example is an amino group wherein the nitrogen atom is substituted by H and tertbutylcarbonyl.

The term "$C_1$-$C_6$-alkyltetrazolyl" denotes a tetrazolyl group wherein one of the nitrogen atoms is substituted by a $C_1$-$C_6$-alkyl group. Particular example is a tetrazolyl group wherein one of the nitrogen atoms is substituted by methyl.

The term "$C_1$-$C_6$-alkyltetrazolyl-$C_1$-$C_6$-alkyl" denotes an $C_1$-$C_6$-alkyl group wherein one of the H atom is replaced by an $C_1$-$C_6$-alkyltetrazolyl group. Particular example is a methyl or a ethyl group wherein one of the the nitrogen atoms is substituted by methyltetrazolyl.

The term "$C_2$-$C_6$-alkynyl" denotes a monovalent linear or branched hydrocarbon group of 2 to 6 carbon atoms with at least one triple bond. In particular embodiments, alkynyl has 2 to 4 carbon atoms with at least one triple bond. Particular example is ethynyl.

The term "amino" denotes a —NH$_2$ group.

The term "cyano" denotes a —C≡N group.

The term "$C_3$-$C_8$-cycloalkoxy" denotes a group of the formula —O—R', wherein R' is a $C_3$-$C_8$-cycloalkyl. Particular example is a group wherein R' is cyclopropyl.

The term "$C_3$-$C_8$-cycloalkoxy-$C_1$-$C_6$-alkyl" denotes a $C_1$-$C_6$-alkyl group wherein at least one of the hydrogen atoms of the $C_1$-$C_6$-alkyl group is replaced by a $C_3$-$C_8$-cycloalkoxy group. Particluar example is a methyl or ethyl group wherein the $C_3$-$C_8$-cycloalkoxy group is cyclopropoxy.

The term "$C_3$-$C_8$-cycloalkyl" denotes a monovalent saturated monocyclic or bicyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic $C_3$-$C_8$-cycloalkyl are bicyclo[2.2.1]heptanyl or bicyclo[2.2.2]octanyl. Particular $C_{3-8}$-cycloalkyl group is cyclopropyl.

The term "$C_1$-$C_6$-alkoxy" denotes a group of the formula —O—R', wherein R' is a $C_1$-$C_6$-alkyl group. Examples of $C_1$-$C_6$-alkoxy group include methoxy, ethoxy, n-propoxy, isopropoxy, n-butoxy, isobutoxy and tert-butoxy.

The term "$C_3$-$C_8$-cycloalkyl-$C_1$-$C_6$-alkoxy" denotes a $C_1$-$C_6$-alkoxy group wherein at least one of the hydrogen atoms of the $C_1$-$C_6$-alkoxy group is replaced by a $C_3$-$C_8$-cycloalkyl group.

Particular examples are methoxy or ethoxy goups wherein at least one of the hydrogen atoms of is replaced by a cyclopropyl.

The term "$C_3$-$C_8$-cycloalkylcarbonyl" denotes a group of the formula —C(O)—R', wherein R' is a $C_3$-$C_8$-cycloalkyl group. Examples of $C_3$-$C_8$-cycloalkylcarbonyl are groups wherein R' is cyclopropyl.

The term "$C_3$-$C_8$-cycloalkylcarbonylamino" denotes an amino group wherein the nitrogen atom is substituted by one H atom and by a $C_3$-$C_8$-cycloalkylcarbonyl group. Particular example is an amino group wherein the nitrogen atom is substituted by a H and a cyclopropyl.

The term "halo-$C_1$-$C_6$-alkoxy" denotes a $C_1$-$C_6$-alkoxy group wherein at least one of the hydrogen atoms of the $C_1$-$C_6$-alkoxy group has been replaced by the same or different halogen atoms. Particular examples are difluoromethoxy, trifluoromethoxy, difluoroethoxy and trifluoroethoxy. More particular example is trifluoromethoxy.

The term "halogen" and "halo" are used interchangeably herein and denote fluoro, chloro, bromo or iodo. Particular halogen is chloro.

The term "halo-$C_1$-$C_6$-alkyl" denotes a $C_1$-$C_6$-alkyl group wherein at least one of the hydrogen atoms of the $C_1$-$C_6$-alkyl group has been replaced by the same or different halogen atoms. Particular examples are difluoromethyl, trifluoromethyl, difluoroethyl and trifluoroethyl. More particular example is trifluoromethyl.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular example is tetrahydropyranyl.

The term "heterocycloalkyl-$C_1$-$C_6$-alkoxy" denotes a $C_1$-$C_6$-alkoxy group wherein at least one of the hydrogen atoms of the alkoxy group is replaced by a heterocycloalkyl group. Particular examples are tetrahydropyranylmethoxy.

The term "hydroxy" denotes a —OH group.

The term "hydroxy-$C_1$-$C_6$-alkoxy" denotes a $C_1$-$C_6$-alkoxy group wherein one of the hydrogen atoms of the $C_1$-$C_6$-alkoxy is replaced by a hydroxy group. Particular examples are hydroxyethoxy and hydroxypropoxy.

The term "hydroxy-$C_1$-$C_6$-alkyl" denotes a $C_1$-$C_6$-alkyl group wherein one of the hydrogen atoms of the $C_1$-$C_6$-alkyl group is replaced by a hydroxy group. Particular examples are hydroxymethyl and hydroxyethyl.

The term "phenoxy" denotes a group of the formula —O—R', wherein R' is a phenyl group.

The term "phenoxy-$C_1$-$C_6$-alkyl" denotes a $C_{1-6}$-alkyl group wherein one of the hydrogen atoms of the $C_1$-$C_6$-alkyl group is replaced by a phenoxy group. Particular example is phenoxymethyl.

The term "phenyl-$C_1$-$C_6$-alkyl" denotes a $C_1$-$C_6$-alkyl group wherein one of the hydrogen atoms of the $C_1$-$C_6$-alkyl group is replaced by a phenyl group. Particular example is phenylmethyl.

The term "phenyl-$C_2$-$C_6$-alkenyl" denotes a $C_2$-$C_6$-alkenyl group wherein one of the hydrogen atoms of the $C_2$-$C_6$-alkenyl group is replaced by a phenyl group. Particular example is phenylethylenyl.

The term "phenyl-$C_2$-$C_6$-alkynyl" denotes a $C_2$-$C_6$-alkynyl group wherein one of the hydrogen atoms of the $C_2$-$C_6$-alkynyl group is replaced by a phenyl group. Particular example is phenylethynyl.

The term "pyridinyl-$C_1$-$C_6$-alkyl" denotes a $C_1$-$C_6$-alkyl group wherein one of the hydrogen atoms of the $C_1$-$C_6$-alkyl group is replaced by a pyridinyl group. Particular example is pyridinylmethyl.

The term "pyridinyl-$C_2$-$C_6$-alkenyl" denotes a $C_2$-$C_6$-alkenyl group wherein one of the hydrogen atoms of the $C_2$-$C_6$-alkenyl group is replaced by a pyridinyl group. Particular example is pyridinylethylenyl.

The term "pyridinyl-$C_2$-$C_6$-alkynyl" denotes a $C_2$-$C_6$-alkynyl group wherein one of the hydrogen atoms of the $C_2$-$C_6$-alkynyl group is replaced by a pyridinyl group. Particular example is pyridinylethynyl.

The term "thiophenyl-$C_1$-$C_6$-alkyl" denotes a $C_1$-$C_6$-alkyl group wherein one of the hydrogen atoms of the $C_1$-$C_6$-alkyl group is replaced by a thiophenyl group. Particular example is thiophenylmethyl.

The term "thiophenyl-$C_2$-$C_6$-alkenyl" denotes a $C_2$-$C_6$-alkenyl group wherein one of the hydrogen atoms of the $C_2$-$C_6$-alkenyl group is replaced by a thiophenyl group. Particular example is thiophenylethenyl.

The term "thiophenyl-$C_2$-$C_6$-alkynyl" denotes a $C_2$-$C_6$-alkynyl group wherein one of the hydrogen atoms of the $C_2$-$C_6$-alkynyl group is replaced by a thiophenyl group. Particular example is thiophenylethynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention provides compounds according to formula (I) or (II) as described herein, wherein $R^1$ is selected from the groups consisting of
i) phenyl-$C_{1-6}$-alkyl substituted by $R^3$, $R^4$ and $R^5$,
ii) pyridinyl substituted by $R^3$, $R^4$ and $R^5$, and
iii) pyridinyl-$C_{1-6}$-alkyl substituted by $R^3$, $R^4$ and $R^5$;
Y is selected from the groups consisting of
i) —OC(O)—, and
ii) —C(O)—;
A is selected from the groups consisting of
i) —O—, and
ii) —S—;
X is selected from the groups consisting of
i) —N—, and
ii) —CH—;

W is —C(O)—;

R² is selected from the ring systems O, AO and AW;

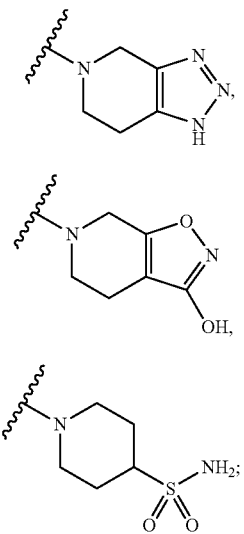

R³ is selected from the groups consisting of
i) $C_{1-6}$-alkylcarbonylamino, and
ii) tetrahydropyranyl-$C_{1-6}$-alkoxy;

R⁴ is selected from the groups consisting of
i) cyano,
ii) $C_{3-8}$-cycloalkyl, and
iii) halo-$C_{1-6}$-alkyl;

R⁵ is selected from the groups consisting of
i) H, and
ii) halogen;

m and n are independently selected from 1 and 2;

or pharmaceutically acceptable salts.

A particular embodiment of the present invention provides compounds according to formula (I) or (II) as described herein, wherein R¹ is selected from the group consisting of
i) phenyl-$C_{1-6}$-alkyl substituted by R³, R⁴ and R⁵,
ii) pyridinyl substituted by R³, R⁴ and R⁵, and
iii) pyridinyl-$C_{1-6}$-alkyl substituted by R³, R⁴ and R⁵.

Another embodiment of the present invention provides compounds according to formula (I) as described herein, wherein R¹ is selected from the group consisting of
i) phenyl-$C_{1-6}$-alkyl substituted by R³, R⁴ and R⁵, and
ii) pyridinyl substituted by R³, R⁴ and R⁵.

A particular embodiment of the present invention provides compounds according to formula (I) as described herein, wherein Y is selected from the groups consisting of
i) —OC(O)—, and
ii) —C(O)—.

A more particular embodiment of the present invention provides compounds according to formula (I) as described herein, wherein A is selected from the groups consisting of
i) —O—, and
ii) —S—.

A furthermore particular embodiment of the present invention provides compounds according to formula (I) as described herein, wherein A is —O—.

A furthermore particular embodiment of the present invention provides compounds according to formula (I) as described herein, wherein X is —N—.

Another furthermore particular embodiment of the present invention provides compounds according to formula (I) as described herein, wherein W is —C(O)—.

Another furthermore particular embodiment of the present invention provides compounds according to formula (I) as described herein, wherein X is selected from the groups consisting of
i) —N—, and
ii) —CH—.

Another furthermore particular embodiment of the present invention provides compounds according to formula (I) as described herein, wherein R² is selected from the ring systems O, AO and AW.

Another furthermore particular embodiment of the present invention provides compounds according to formula (I) as described herein, wherein R² is selected from the ring systems O and AO.

Another furthermore particular embodiment of the present invention provides compounds according to formula (I) as described herein, wherein R³ is selected from the groups consisting of
i) $C_{1-6}$-alkylcarbonylamino, and
ii) tetrahydropyranyl-$C_{1-6}$-alkoxy.

Another furthermore particular embodiment of the present invention provides compounds according to formula (I) as described herein, wherein R⁴ is selected from the groups consisting of
i) cyano,
ii) $C_{3-8}$-cycloalkyl, and
iii) halo-$C_{1-6}$-alkyl.

Another furthermore particular embodiment of the present invention provides compounds according to formula (I) as described herein, wherein R⁴ is selected from the groups consisting of
i) cyano, and
ii) $C_{3-8}$-cycloalkyl.

Another furthermore particular embodiment of the present invention provides compounds according to formula (I) as described herein, wherein R⁵ is selected from the groups consisting of
i) H, and
ii) halogen.

Another furthermore particular embodiment of the present invention provides compounds according to formula (I) as described herein, wherein m and n are independently selected from 1 and 2.

Another furthermore particular embodiment of the present invention provides compounds according to formula (I) as described herein, wherein m and n are both 1.

A particular embodiment of the present invention provides compounds according to formula I(a) as described herein, wherein R¹ is selected from the groups consisting of
i) phenyl-$C_{1-6}$-alkyl substituted by R³, R⁴ and R⁵, and
ii) pyridinyl substituted by R³, R⁴ and R⁵;

Y is selected from the groups consisting of
iii) —OC(O)—, and
iv) —C(O)—;

A is —O—;

X is N;

W is —C(O)—;

R² is selected from the ring systems O and AO;

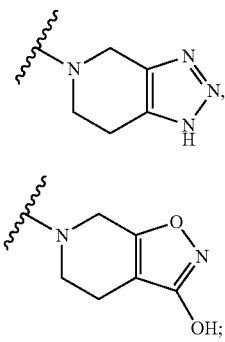

R³ is selected from the groups consisting of
i) C₁₋₆-alkylcarbonylamino, and
ii) tetrahydropyranyl-C₁₋₆-alkoxy;
R⁴ is selected from the groups consisting of
i) cyano, and
ii) C₃₋₈-cycloalkyl;
R⁵ is selected from the groups consisting of
i) H, and
ii) halogen;
m and n are both 1;
or pharmaceutically acceptable salts.

A particular embodiment of the present invention provides compounds according to formula (I) as described herein.

A particular embodiment of the present invention provides compounds according to formula (II) as described herein.

A particular embodiment of the present invention provides compounds according to formula (I) as described herein, wherein
R¹ is selected from the groups consisting of
i) pyridinyl substituted by R³, R⁴ and R⁵, and
ii) pyridinyl-C₁₋₆-alkyl substituted by R³, R⁴ and R⁵;
Y is selected from the groups consisting of
i) —OC(O)—, and
ii) —C(O)—;
W is —C(O)—;
R² is selected from the ring systems O, AO and AW;

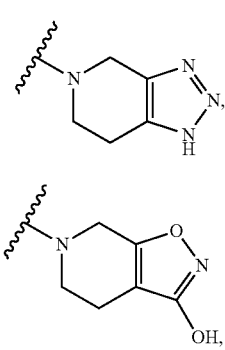

R³ is selected from the groups consisting of
i) C₁₋₆-alkylcarbonylamino, and
ii) tetrahydropyranyl-C₁₋₆-alkoxy;
R⁴ is selected from the groups consisting of
i) C₃₋₈-cycloalkyl, and
ii) halo-C₁₋₆-alkyl;
R⁵ is H;
m is selected from 1 and 2;
n is 1;
or pharmaceutically acceptable salts.

A particular embodiment of the present invention provides compounds according to formula (I) as described herein, wherein
wherein
R¹ is pyridinyl substituted by R³, R⁴ and R⁵;
Y is —C(O)—;
W is —C(O)—;
R² is selected the ring systems O;

R³ is tetrahydropyranyl-C₁₋₆-alkoxy;
R⁴ is C₃₋₈-cycloalkyl;
R⁵ is H;
m and n are both 1;
or pharmaceutically acceptable salts.

A particular embodiment of the present invention provides compounds according to formula (II) as described herein, wherein
R¹ is selected from the groups consisting of
i) phenyl-C₁₋₆-alkyl substituted by R³, R⁴ and R⁵,
ii) pyridinyl substituted by R³, R⁴ and R⁵, and
iii) pyridinyl-C₁₋₆-alkyl substituted by R³, R⁴ and R⁵;
Y is selected from the groups consisting of
i) —OC(O)—, and
ii) —C(O)—;
A is selected from the groups consisting of
i) —O—, and
ii) —S—;
X is selected from the groups consisting of
i) —N—, and
ii) —CH—;
W is —C(O)—;
R² is selected from the ring systems O, AO and AW;

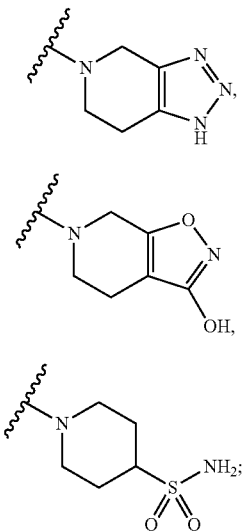

R³ is selected from the groups consisting of
i) C₁₋₆-alkylcarbonylamino, and
ii) tetrahydropyranyl-C₁₋₆-alkoxy;
R⁴ is selected from the groups consisting of
i) cyano,
ii) C₃₋₈-cycloalkyl, and
iii) halo-C₁₋₆-alkyl;
R⁵ is selected from the groups consisting of
i) H, and
ii) halogen;
m is 1;
n is selected from 1 and 2;
or pharmaceutically acceptable salts.

A particular embodiment of the present invention provides compounds according to formula (II) as described herein, wherein
R¹ is selected from the groups consisting of
i) phenyl-C₁₋₆-alkyl substituted by R³, R⁴ and R⁵, and
ii) pyridinyl substituted by R³, R⁴ and R⁵;
Y is selected from the groups consisting of
i) —OC(O)—, and
ii) —C(O)—;
A is —O—;
X is —N—;
W is —C(O)—;
R² is selected from the ring systems O and AO;

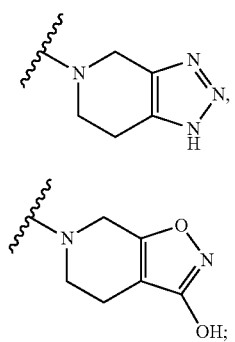

R³ is selected from the groups consisting of
i) C₁₋₆-alkylcarbonylamino, and
ii) tetrahydropyranyl-C₁₋₆-alkoxy;
R⁴ is selected from the groups consisting of
i) cyano, and
ii) C₃₋₈-cycloalkyl;
R⁵ is selected from the groups consisting of
i) H, and
ii) halogen;
m and n are both 1;
or pharmaceutically acceptable salts.

Particular examples of compounds of formula (I) as described herein are selected from
[2-[2-cyclopropyl-6-(oxan-4-ylmethoxy)pyridine-4-carbonyl]-3,4-dihydro-1H-isoquinolin-6-yl]-(1,4,6,7-tetrahydrotriazolo[4,5-c]pyridin-5-yl)methanone;
[2-cyclopropyl-6-(oxan-4-ylmethoxy)pyridin-4-yl]-[2-(1,4,6,7-tetrahydrotriazolo[4,5-c]pyridine-5-carbonyl)-4,6-dihydropyrrolo[3,4-d][1,3]oxazol-5-yl]methanone;
[2-[2-cyclopropyl-6-(oxan-4-ylmethoxy)pyridine-4-carbonyl]-1,3-dihydroisoindol-5-yl]-(1,4,6,7-tetrahydrotriazolo[4,5-c]pyridin-5-yl)methanone;
[2-cyclopropyl-6-(oxan-4-ylmethoxy)pyridin-4-yl]-[2-(1,4,6,7-tetrahydrotriazolo[4,5-c]pyridine-5-carbonyl)-6,7-dihydro-4H-[1,3]thiazolo[5,4-c]pyridin-5-yl]methanone;
[2-[2-cyclopropyl-6-(oxan-4-ylmethoxy)pyridine-4-carbonyl]-1,3-dihydroisoindol-5-yl]-(3-hydroxy-5,7-dihydro-4H-[1,2]oxazolo[5,4-c]pyridin-6-yl)methanone;
1-[2-[2-cyclopropyl-6-(oxan-4-ylmethoxy)pyridine-4-carbonyl]-1,3-dihydroisoindole-5-carbonyl]piperidine-4-sulfonamide;
[2-[2-cyclopropyl-6-(oxan-4-ylmethoxy)pyridine-4-carbonyl]-1,3-dihydroisoindol-5-yl]-(3-hydroxy-6,7-dihydro-4H-[1,2]oxazolo[4,5-c]pyridin-5-yl)methanone;
[3-(2,2-dimethylpropanoylamino)-5-(trifluoromethyl)pyridin-2-yl]methyl 5-(4-sulfamoylpiperidine-1-carbonyl)-1,3-dihydroisoindole-2-carboxylate;
[3-(2,2-dimethylpropanoylamino)-5-(trifluoromethyl)pyridin-2-yl]methyl 5-(3-hydroxy-5,7-dihydro-4H-[1,2]oxazolo[5,4-c]pyridine-6-carbonyl)-1,3-dihydroisoindole-2-carboxylate;
[3-(2,2-dimethylpropanoylamino)-5-(trifluoromethyl)pyridin-2-yl]methyl 5-(3-hydroxy-6,7-dihydro-4H-[1,2]oxazolo[4,5-c]pyridine-5-carbonyl)-1,3-dihydroisoindole-2-carboxylate;
[3-(2,2-dimethylpropanoylamino)-5-(trifluoromethyl)pyridin-2-yl]methyl 2-(4-sulfamoylpiperidine-1-carbonyl)-4,6-dihydropyrrolo[3,4-d][1,3]oxazole-5-carboxylate;
[2-cyclopropyl-6-(oxan-4-ylmethoxy)pyridin-4-yl]-[2-(3-hydroxy-5,7-dihydro-4H-[1,2]oxazolo[5,4-c]pyridine-6-carbonyl)-4,6-dihydropyrrolo[3,4-d][1,3]oxazol-5-yl]methanone;
1-[5-[2-cyclopropyl-6-(oxan-4-ylmethoxy)pyridine-4-carbonyl]-4,6-dihydropyrrolo[3,4-d][1,3]thiazole-2-carbonyl]piperidine-4-sulfonamide;
1-[5-[2-cyclopropyl-6-(oxan-4-ylmethoxy)pyridine-4-carbonyl]-4,6-dihydrothieno[2,3-c]pyrrole-2-carbonyl]piperidine-4-sulfonamide;
[3-(2,2-dimethylpropanoylamino)-5-(trifluoromethyl)pyridin-2-yl]methyl 2-(1,4,6,7-tetrahydrotriazolo[4,5-c]pyridine-5-carbonyl)-4,6-dihydropyrrolo[3,4-d][1,3]oxazole-5-carboxylate;
[5-chloro-4-cyano-2-(2,2-dimethylpropanoylamino)phenyl]methyl 2-(3-hydroxy-5,7-dihydro-4H-[1,2]oxazolo[5,4-c]pyridine-6-carbonyl)-4,6-dihydropyrrolo[3,4-d][1,3]oxazole-5-carboxylate;

[3-(2,2-dimethylpropanoylamino)-5-(trifluoromethyl)pyridin-2-yl]methyl 2-(4-sulfamoylpiperidine-1-carbonyl)-4,6-dihydrothieno[2,3-c]pyrrole-5-carboxylate;
and pharmaceutically acceptable salts thereof.

Further particular examples of compounds of formula (I) as described herein are selected from
[2-cyclopropyl-6-(oxan-4-ylmethoxy)pyridin-4-yl]-[2-(1,4,6,7-tetrahydrotriazolo[4,5-c]pyridine-5-carbonyl)-4,6-dihydropyrrolo[3,4-d][1,3]oxazol-5-yl]methanone;
[2-[2-cyclopropyl-6-(oxan-4-ylmethoxy)pyridine-4-carbonyl]-1,3-dihydroisoindol-5-yl]-(1,4,6,7-tetrahydrotriazolo[4,5-c]pyridin-5-yl)methanone;
[2-cyclopropyl-6-(oxan-4-ylmethoxy)pyridin-4-yl]-[2-(3-hydroxy-5,7-dihydro-4H-[1,2]oxazolo[5,4-c]pyridine-6-carbonyl)-4,6-dihydropyrrolo[3,4-d][1,3]oxazol-5-yl]methanone;
[5-chloro-4-cyano-2-(2,2-dimethylpropanoylamino)phenyl] methyl 2-(3-hydroxy-5,7-dihydro-4H-[1,2]oxazolo[5,4-c]pyridine-6-carbonyl)-4,6-dihydropyrrolo[3,4-d][1,3]oxazole-5-carboxylate;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I) can be synthesised from amine precursor 1 and appropriate reagents, using methods well known in the art.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

The present invention provides novel compounds of formula (I) or (II)

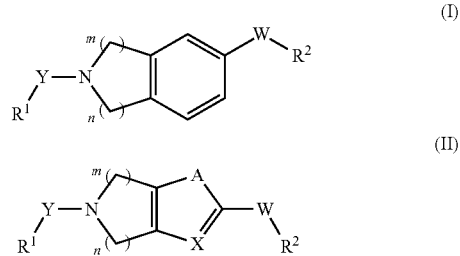

Compounds of general formula (I) can be synthesised from amine precursor 1 and appropriate reagents, using methods well known in the art.

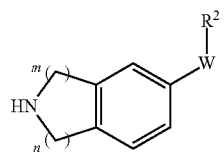

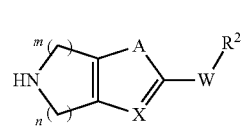

For instance, amine 1A or 1B is reacted with a suitable carboxylic acid of formula $R^1$—COOH (2) leading to a compound of formula (I) and (II), respectively, wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1A or 1B can also be reacted with suitable acylating reagents such as acyl chlorides of formula $R^1$—COCl (3) to lead to compounds of formula (I) and (II), respectively, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 1A or 1B is reacted with a suitable chloroformate ester of formula $R^1$—O—C(O)—Cl (4), or with an imidazole-1-carboxylate ester of formula (5), leading to a compound of formula (I) and (II), respectively, wherein Y is —OC(O)—.

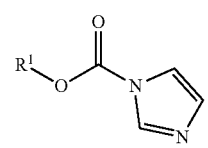

The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Chloroformate esters 4 are commercially available or can be synthesised from the corresponding alcohol of formula R¹—OH, by reaction with phosgene or a phosgene equivalent (e. g., diphosgene, triphosgene), as described in the literature.

Imidazole-1-carboxylate esters 5 are synthesised from the corresponding alcohols of formula R¹—OH, by reaction with 1,1'-carbonyldiimidazole. The reaction is performed at room temperature, in a solvent such as dichloromethane, tetrahydrofuran or acetonitrile. The imidazole-1-carboxylate esters 5 are typically not isolated but directly reacted with amines 1A or 1B as described above.

Alcohols of formula R¹—OH are commercially available or can be produced by methods described herein or known in the art.

Carboxylic acids (2) and acyl halides (3) are commercially available or can be prepared as described herein or in the literature.

Amines of general formula 1A are synthesised from suitably protected precursors 6A. Similarly, amines of general formula 1B are synthesised from suitably protected precursors 6B.

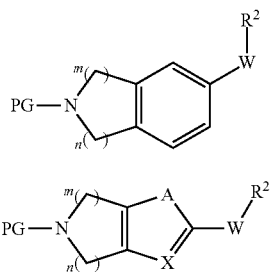

6A

6B

Suitable protective groups (PG) are tert-butoxycarbonyl or benzyloxycarbonyl. The deprotection of intermediates 6A or 6B can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane at temperatures between 0° C. and 30° C.

Carbamates 6A wherein W is —C(O)— are represented by general formula 6AA. Carbamates 6B wherein W is —C(O)— are represented by general formula 6BA. R², m and n are as defined above.

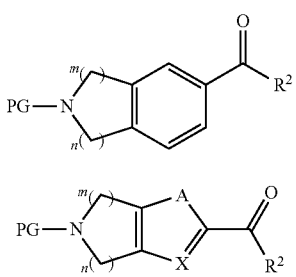

6AA

6BA

Amide 6AA is produced from carboxylic acid 7AA by coupling reaction with an amine of formula H—O, H-AO, H-AW, H-AX, H-AY or H-AZ. Similarly, amide 6BA is produced from carboxylic acid 7BA by coupling reaction with an amine of formula H—O, H-AO, H-AW, H-AX, H-AY or H-AZ.

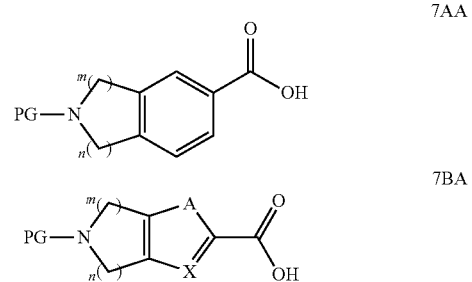

7AA

7BA

The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 7AA and 7BA are commercially available or can be produced as described herein or in the literature.

Carbamates 6A wherein W is —S(O)₂— are represented by general formula 6AB. Carbamates 6B wherein W is —S(O)₂— are represented by general formula 6BB. R², m and n are as defined above.

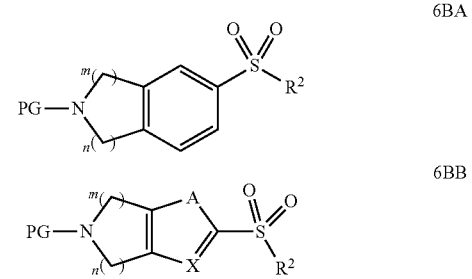

6BA

6BB

Sulfonamide 6BA is produced from sulfonyl chloride 7BA by reaction with an amine of formula H—O, H-AO, H-AW, H-AX, H-AY or H-AZ. Similarly, sulfonamide 6BB is produced from sulfonyl chloride 7BB by reaction with an amine of formula H—O, H-AO, H-AW, H-AX, H-AY or H-AZ. The reaction is performed in the presence of a base, e. g., pyridine or triethylamine, in a suitable solvent, e. g., dichloromethane, tetrahydrofuran or N,N-dimethylformamide, at temperatures between −20° C. and +50° C.

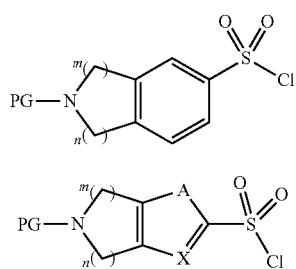

7BA

7BB

Sulfonyl chlorides 7BA and 7BB are commercially available or can be produced as described in the literature.

Compounds of formula (I), wherein W is —C(O)— are represented by general formula 8A. Compounds of formula (II), wherein W is —C(O)— are represented by general formula 8B. $R^1$, $R^2$, m and n are as defined above.

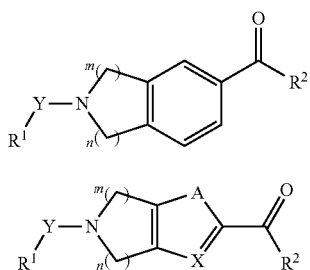

8A

8B

Amide 8A can also be produced from carboxylic acid 9A by coupling reaction with an amine of formula H—O, H-AO, H-AW, H-AX, H-AY or H-AZ, using methods known in the art Similarly, amide 8B is produced from carboxylic acid 9B by coupling reaction with an amine of formula H—O, H-AO, H-AW, H-AX, H-AY or H-AZ.

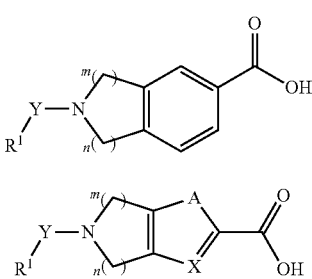

9A

9B

For instance, this reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, the reaction is performed in two steps wherein carboxylic acid 9A or 9B is first converted to acid chloride 10A or 10B, using methods and reagents known in the art, e. g., thionyl chloride or oxalyl chloride. Acid chloride 10A or 10B is then reacted with an amine of formula H—O, H-AO, H-AW, H-AX, H-AY or H-AZ, in a suitable solvent, e. g., dichloromethane, acetonitrile, or N,N-dimethylformamide, in the presence of a base, e. g., triethylamine, pyridine and/or 4-(dimethylamino)pyridine, at temperatures between −40° C. and +100° C.

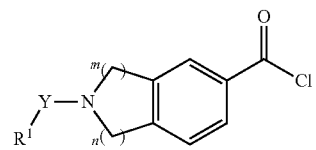

10A

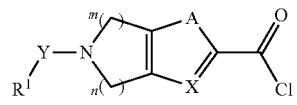

10B

Carboxylic acids 10A can be produced from the corresponding ester precursors 11A, $R^a$ is lower alkyl, e. g. methyl, ethyl, or tert-butyl, using methods and reagents known in the art. Similarly, carboxylic acids 10A can be produced from the corresponding ester precursors 11B. wherein $R^a$ is lower alkyl, e. g. methyl or ethyl, using methods and reagents known in the art. For instance, in the case where $R^a$ is methyl or ethyl, the reaction is performed in the presence of a base, e. g., potassium hydroxide, sodium hydroxide, or lithium hydroxide, in solvents such as water, methanol, ethanol, tetrahydrofuran, or mixtures thereof, at temperatures between 20° C. and 100° C. Alternatively, in the case where $R^a$ is tert-butyl, the reaction is performed in the presence of acid, e. g., formic acid, hydrochloric acid, or trifluoroacetic acid, optionally in the presence of a suitable solvent, e. g., methanol, 2-propanol, or dichloromethane.

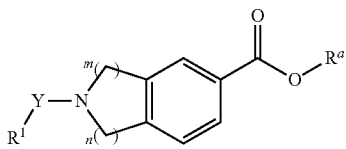

11A

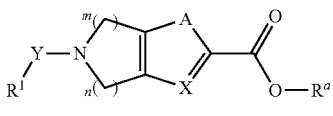

11B

Compounds of formula 11A can be synthesised from amine precursors of formula 12A and appropriate reagents, using methods well known in the art. Similarly, compounds of formula 11B can be synthesised from amine precursors of formula 12B and appropriate reagents, using methods well known in the art.

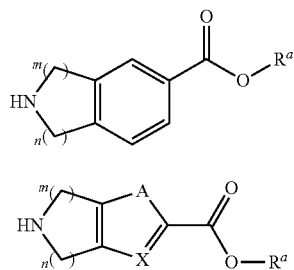

For instance, amine 12A is reacted with a suitable carboxylic acid of formula $R^1$—COOH (2) leading to compounds of formula 11A, wherein Y is —C(O)—. Similarly, amine 12B is reacted with a suitable carboxylic acid of formula $R^1$—COOH (2) leading to compounds of formula 11B, respectively, wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 12A can also be reacted with suitable acylating reagents, such as acyl chlorides of formula $R^1$—COCl (3) to lead to compounds of formula 11A, wherein Y is —C(O)—. Amine 12B can also be reacted with suitable acylating reagents, such as acyl chlorides of formula $R^1$COCl (3) to lead to compounds of formula 11B, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 12A is reacted with a suitable chloroformate ester of formula $R^1$—O—C(O)—Cl (4), or with an imidazole-1-carboxylate ester of formula 5, leading to a compound of formula 11A, wherein Y is —OC(O)—. Similarly, amine 12B is reacted with a suitable chloroformate ester of formula $R^1$—O—C(O)—Cl (4), or with an imidazole-1-carboxylate ester of formula 5, leading to a compound of formula 11B, wherein Y is —OC(O)—. The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Alternatively, amine 12A can be reacted with a phosgene or a phosgene equivalent (e. g., triphosgene) to the corresponding N-chlorocarbonylamine 13A, in the presence of a base (e. g., pyridine) in a suitable solvent, e. g., dichloromethane, at temperatures between −78° C. and +20° C. N-Chlorocarbonylamine 13A is then reacted with alcohol of formula $R^1$—OH, leading to a compound of formula 11A, wherein Y is —OC(O)—. Similarly, amine 12B can be reacted with a phosgene or a phosgene equivalent (e. g., triphosgene) to the corresponding N-chlorocarbonylamine 13B, in the presence of a base (e. g., pyridine) in a suitable solvent, e. g., dichloromethane, at temperatures between −78° C. and +20° C. N-Chlorocarbonylamine 13B is then reacted with alcohol of formula $R^1$—OH, leading to a compound of formula 11B, wherein Y is —OC(O)—. This reaction is performed in a suitable solvent (e. g., acetonitrile of dichloromethane) in the presence of a suitable base (e. g., sodium hydride, pyridine or polystyrene-bound 2-tert-butyl-imino-2-diethylamino-1,3-dimethylperhydro-1,3,2-diazaphosphorine), at temperatures between 20° C. and the boiling point of the solvent.

Amines of general formula 12A are synthesised from suitably protected precursors 14A. Similarly, amines of general formula 12B are synthesised from suitably protected precursors 14A.

Suitable protective groups (PG) are tert-butoxycarbonyl or benzyloxycarbonyl. The deprotection of intermediates 14A and 14B can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C., in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane, at temperatures between 0° C. and 30° C.

Esters 14A, and 14B are commercially available or can be produced by methods described herein or in the literature.

Also an embodiment of the present invention is a process to prepare a compound of formula (I) as defined above comprising the reaction of a compound formula (II) or (III) in the presence of a compound of formula (IV), wherein $R^1$, $R^2$, Y, W, A, X, m and n are as defined herein and in case Y is —C(O)—, then G is halogen or hydoxy and in case Y is —OC(O)—, then G is chloro.

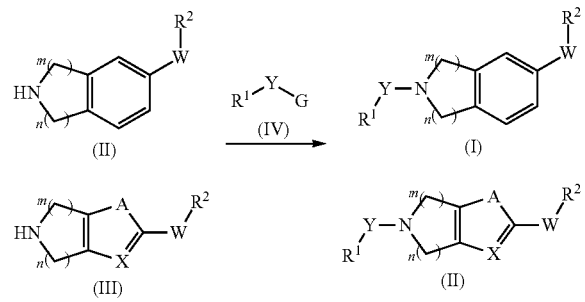

In particular, in the presence of a base, in a solvent such as dichloromethane or dimethylformamide and at a temperature comprised between 0° C. and reflux, particularly between room temperature and reflux and in the presence of a coupling agent.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis of ocular conditions, particularly glaucoma.

The present invention also relates to the use of a compound according to formula (I) as described herein for the preparation of a medicament for the treatment or prophylaxis of ocular conditions, particularly glaucoma.

Also an object of the invention is a method for the treatment or prophylaxis of ocular conditions, particularly glaucoma, which method comprises administering an effective amount of a compound according to formula (I) as described herein.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

Also an embodiment of the present invention provides compounds of formula (I) as described herein, when manufactured according to any one of the described processes.

Assay Procedures

Production of Human Full Length ATX, with and without HIS Tag

Autotaxin (ATX—ENPP2) cloning: cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation: Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19,1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification: 20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy-}ethoxy)-propionylamino]-ethoxy}-hydroxy-phosphoryloxy)-2-hydroxypropyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row O. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C.

Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

| Example | ATX $IC_{50}$ [µM] |
|---|---|
| 1 | 0.002 |
| 1.01 | 0.002 |
| 1.02 | 0.008 |
| 1.03 | 0.005 |
| 2 | 0.024 |
| 2.01 | 0.01 |
| 2.02 | 0.007 |
| 2.03 | 0.007 |
| 2.04 | 0.007 |
| 2.05 | 0.004 |
| 2.06 | 0.001 |
| 3 | 0.005 |
| 3.01 | 0.002 |
| 3.02 | 0.007 |
| 4 | 0.001 |
| 4.01 | 0.007 |
| 4.02 | 0.001 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Example 1

[2-[2-Cyclopropyl-6-(oxan-4-ylmethoxy)pyridine-4-carbonyl]-3,4-dihydro-1H-isoquinolin-6-yl]-(1,4,6,7-tetrahydrotriazolo[4,5-c]pyridin-5-yl)methanone

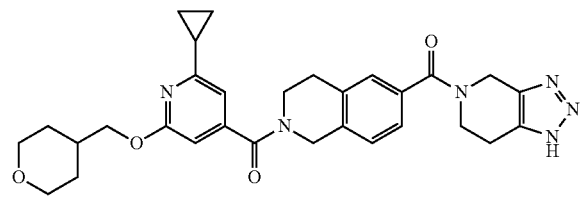 [SMILES: O=C(c1cc(OCC2CCOCC2)nc(C2CC2)c1)N1CCc2cc(C(=O)N3CCc4[nH]nnc4C3)ccc2C1]

To a solution of 1,2,3,4-tetrahydroisoquinolin-6-yl(1,4,6,7-tetrahydrotriazolo[4,5-c]pyridin-5-yl)methanone; hydrochloride (intermediate 1; 50 mg, 156 µmol) in N,N-dimethylformamide (4 ml) was added 4-methylmorpholine (94.9 mg, 938 µmol), 2-cyclopropyl-6-(oxan-4-ylmethoxy)pyridine-4-carboxylic acid (CAS-RN 1810776-23-8; 43.4 mg, 156 µmol) and O-(7-azabenzotriazol-1-yl)-N,N,N',N'-tetramethyluronium hexafluoro-phosphate (59.5 mg, 156 µmol) at room temperature, then after 16 h the reaction mixture was partitioned between sat. aq. sodium hydrogen carbonate solution and a mixture of ethyl acetate and 2-methyltetrahydrofuran. The organic layer was washed with ammonium chloride solution and brine, dried over magnesium sulfate, filtered and evaporated. Chromatography (silica gel, gradient dichloromethane to dichloromethane/methanol/25% aq. ammonia solution 90:10:2.5) produced the title compound (71 mg, 84%). White foam, MS: 543.4 (M+H)$^+$.

The following examples were prepared according to example 1, replacing 1,2,3,4-tetrahydroisoquinolin-6-yl(1,4,6,7-tetrahydrotriazolo[4,5-c]pyridin-5-yl)methanone; hydrochloride by the appropriate amine and 2-cyclopropyl-6-(oxan-4-ylmethoxy)pyridine-4-carboxylic acid by the appropriate carboxylic acid.

| Ex. | Systematic Name | Amine/Carboxylic acid | MS, m/e |
|---|---|---|---|
| 1.01 | [2-cyclopropyl-6-(oxan-4-ylmethoxy)pyridin-4-yl]-[2-(1,4,6,7-tetrahydrotriazolo[4,5-c]pyridine-5-carbonyl)-4,6-dihydropyrrolo[3,4-d][1,3]oxazol-5-yl]methanone | 5,6-dihydro-4H-pyrrolo[3,4-d][1,3]oxazol-2-yl(1,4,6,7-tetrahydrotriazolo[4,5-c]pyridin-5-yl)methanone; hydrochloride (intermediate 1.1)/2-cyclopropyl-6-(oxan-4-ylmethoxy)pyridine-4-carboxylic acid (CAS-RN 1810776-23-8) | 518.4 (M − H)$^-$ |

| Ex. | Systematic Name | Amine/Carboxylic acid | MS, m/e |
|---|---|---|---|
| 1.02 | [2-[2-cyclopropyl-6-(oxan-4-ylmethoxy)pyridine-4-carbonyl]-1,3-dihydroisoindol-5-yl]-(1,4,6,7-tetrahydrotriazolo[4,5-c]pyridin-5-yl)methanone | 2,3-dihydro-1H-isoindol-5-yl(1,4,6,7-tetrahydrotriazolo[4,5-c]pyridin-5-yl)methanone; hydrochloride (intermediate 1.2)/2-cyclopropyl-6-(oxan-4-ylmethoxy)pyridine-4-carboxylic acid (CAS-RN 1810776-23-8) | 529.3 (M + H)+ |
| 1.03 | [2-cyclopropyl-6-(oxan-4-ylmethoxy)pyridin-4-yl]-[2-(1,4,6,7-tetrahydrotriazolo[4,5-c]pyridine-5-carbonyl)-6,7-dihydro-4H-[1,3]thiazolo[5,4-c]pyridin-5-yl]methanone | 4,5,6,7-tetrahydro-[1,3]thiazolo[5,4-c]pyridin-2-yl(1,4,6,7-tetrahydrotriazolo[4,5-c]pyridin-5-yl)methanone; hydrochloride (intermediate 1.3)/2-cyclopropyl-6-(oxan-4-ylmethoxy)pyridine-4-carboxylic acid (CAS-RN 1810776-23-8) | 550.3 (M + H)+ |

Example 2

[2-[2-Cyclopropyl-6-(oxan-4-ylmethoxy)pyridine-4-carbonyl]-1,3-dihydroisoindol-5-yl]-(3-hydroxy-5,7-dihydro-4H-[1,2]oxazolo[5,4-c]pyridin-6-yl)methanone

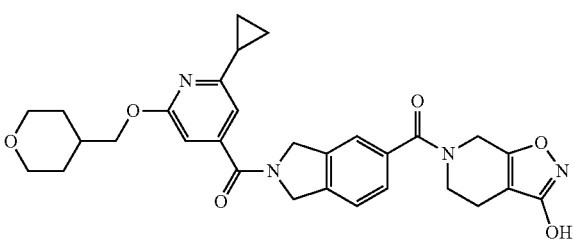 [SMILES: O=C(c1cc(OCC2CCOCC2)nc(C2CC2)c1)N1Cc2ccc(C(=O)N3CCc4c(O)noc4C3)cc2C1]

To a mixture of 2-[2-cyclopropyl-6-(oxan-4-ylmethoxy)pyridine-4-carbonyl]-1,3-dihydroisoindole-5-carboxylic acid (intermediate 2; 60 mg, 142 µmol) in N,N-dimethylformamide (4 ml) was added 4-methylmorpholine (115 mg, 1.14 mmol), 4,5,6,7-tetrahydro-[1,2]oxazolo[5,4-c]pyridin-3-ol; hydrochloride (CAS-RN 64603-91-4; 32.6 mg 184.6 µmol) and O-(7-azabenzotriazol-1-yl)-N,N,N',N'-tetramethyluronium hexafluoro-phosphate (75.6 mg, 198.8 µmol) at room temperature, then after 16 h the reaction mixture was partitioned between sat. aq. ammonium chloride solution and dichloromethane. The organic layer was washed with brine, dried over magnesium sulfate, filtered and evaporated. Chromatography (silica gel, gradient dichloromethane to dichloromethane/methanol 9:1) produced the title compound (46 mg, 61%). Yellow foam, MS: 545.3 (M+H)+.

The following examples were prepared according to example 2, replacing 2-[2-cyclopropyl-6-(oxan-4-ylmethoxy)pyridine-4-carbonyl]-1,3-dihydroisoindole-5-carboxylic acid by the appropriate caboxylic acid and 4,5,6,7-tetrahydro-[1,2]oxazolo[5,4-c]pyridin-3-ol; hydrochloride by the appropriate amine.

| Ex. | Systematic Name | Carboxylic acid/Amine | MS, m/e |
|---|---|---|---|
| 2.01 | 1-[2-[2-cyclopropyl-6-(oxan-4-ylmethoxy)pyridine-4-carbonyl]-1,3-dihydroisoindole-5-carbonyl]piperidine-4-sulfonamide | 2-[2-cyclopropyl-6-(oxan-4-ylmethoxy)pyridine-4-carbonyl]-1,3-dihydroisoindole-5-carboxylic acid (intermediate 2)/piperidine-4-sulfonamide; hydrochloride | 569.3 (M + H)⁺ |
| 2.02 | [2-[2-cyclopropyl-6-(oxan-4-ylmethoxy)pyridine-4-carbonyl]-1,3-dihydroisoindol-5-yl]-(3-hydroxy-6,7-dihydro-4H-[1,2]oxazolo[4,5-c]pyridin-5-yl)methanone | 2-[2-cyclopropyl-6-(oxan-4-ylmethoxy)pyridine-4-carbonyl]-1,3-dihydroisoindole-5-carboxylic acid (intermediate 2)/4,5,6,7-tetrahydro-[1,2]oxazolo[4,5-c]pyridin-3-ol (CAS-RN 53602-00-9) | 545.2 (M + H)⁺ |
| 2.03 | [3-(2,2-dimethylpropanoylamino)-5-(trifluoromethyl)pyridin-2-yl]methyl 5-(4-sulfamoylpiperidine-1-carbonyl)-1,3-dihydroisoindole-2-carboxylate | 2-[[3-(2,2-dimethylpropanoylamino)-5-(trifluoromethyl)pyridin-2-yl]methoxycarbonyl]-1,3-dihydroisoindole-5-carboxylic acid (intermediate 3)/piperidine-4-sulfonamide; hydrochloride | 612.3 (M + H)⁺ |

| Ex. | Systematic Name | Carboxylic acid/Amine | MS, m/e |
|---|---|---|---|
| 2.04 | [3-(2,2-dimethylpropanoylamino)-5-(trifluoromethyl)pyridin-2-yl]methyl 5-(3-hydroxy-5,7-dihydro-4H-[1,2]oxazolo[5,4-c]pyridine-6-carbonyl)-1,3-dihydroisoindole-2-carboxylate 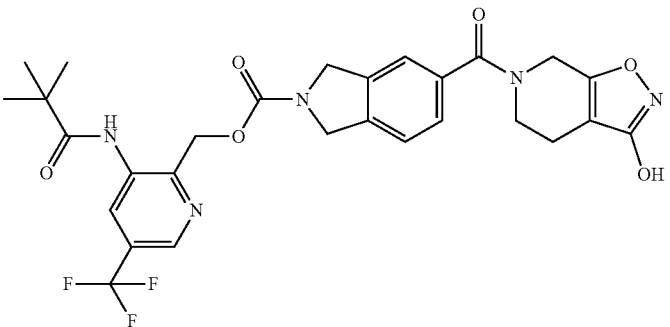 | 2-[[3-(2,2-dimethylpropanoylamino)-5-(trifluoromethyl)pyridin-2-yl]methoxycarbonyl]-1,3-dihydroisoindole-5-carboxylic acid (intermediate 3)/4,5,6,7-tetrahydro-[1,2]oxazolo[5,4-c]pyridin-3-ol; hydrochloride (CAS-RN 64603-91-4) | 588.2 (M + H)⁺ |
| 2.05 | [3-(2,2-dimethylpropanoylamino)-5-(trifluoromethyl)pyridin-2-yl]methyl 5-(3-hydroxy-6,7-dihydro-4H-[1,2]oxazolo[4,5-c]pyridine-5-carbonyl)-1,3-dihydroisoindole-2-carboxylate 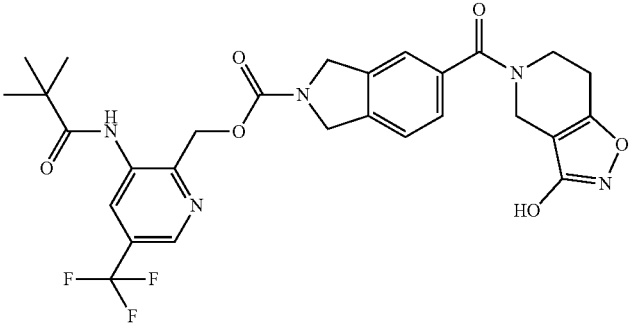 | 2-[[3-(2,2-dimethylpropanoylamino)-5-(trifluoromethyl)pyridin-2-yl]methoxycarbonyl]-1,3-dihydroisoindole-5-carboxylic acid (intermediate 3)/4,5,6,7-tetrahydro-[1,2]oxazolo[4,5-c]pyridin-3-ol (CAS-RN 53602-00-9) | 588.2 (M + H)⁺ |
| 2.06 | [3-(2,2-dimethylpropanoylamino)-5-(trifluoromethyl)pyridin-2-yl]methyl 2-(4-sulfamoylpiperidine-1-carbonyl)-4,6-dihydropyrrolo[3,4-d][1,3]oxazole-5-carboxylate 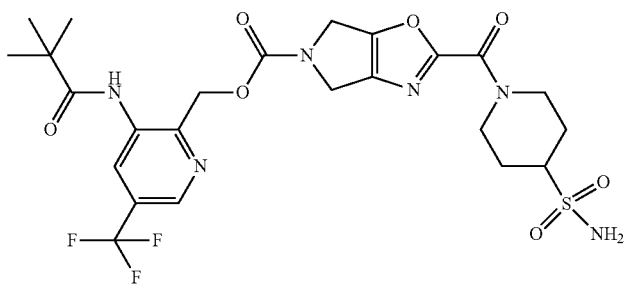 | 5-[[3-(2,2-dimethylpropanoylamino)-5-(trifluoromethyl)pyridin-2-yl]methoxycarbonyl]-4,6-dihydropyrrolo[3,4-d][1,3]oxazole-2-carboxylic acid (intermediate 3.1)/piperidine-4-sulfonamide; hydrochloride | 603.3 (M + H)⁺ |

Example 3

[2-Cyclopropyl-6-(oxan-4-ylmethoxy)pyridin-4-yl]-[2-(3-hydroxy-5,7-dihydro-4H-[1,2]oxazolo[5,4-c]pyridine-6-carbonyl)-4,6-dihydropyrrolo[3,4-d][1,3]oxazol-5-yl]methanone

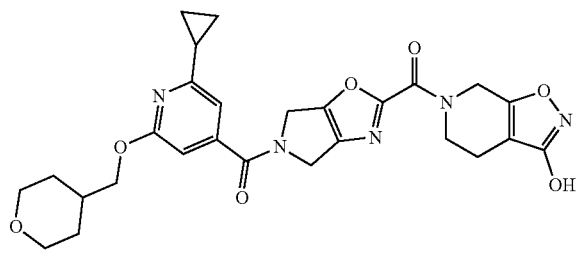 [SMILES: O=C(c1cc(OCC2CCOCC2)nc(C2CC2)c1)N1Cc2nc(C(=O)N3CCc4c(O)noc4C3)oc2C1]

To a mixture of 5,6-dihydro-4H-pyrrolo[3,4-d][1,3]oxazol-2-yl-(3-hydroxy-5,7-dihydro-4H-[1,2]oxazolo[5,4-c]pyridin-6-yl)methanone; hydrochloride (intermediate 4; 60 mg, 173 µmol) in N,N-dimethylformamide (4 ml) was added 4-methylmorpholine (140 mg, 1.38 mmol), 2-cyclopropyl-6-(oxan-4-ylmethoxy)pyridine-4-carboxylic acid (CAS-RN 1810776-23-8; 47.9 mg 173 µmol) and O-(7-azabenzotriazol-1-yl)-N,N,N',N'-tetramethyluronium hexafluoro-phosphate (65.7 mg, 173 µmol) at room temperature, then after 16 h the reaction mixture was partitioned between sat. aq. ammonium chloride solution and dichloromethane. The organic layer was washed with brine, dried over magnesium sulfate, filtered and evaporated. Chromatography (silica gel, gradient dichloromethane to dichloromethane/methanol 9:1) produced the title compound (40 mg, 43%). Light yellow foam, MS: 536.3 (M+H)$^+$.

The following examples were prepared according to example 3, replacing 5,6-dihydro-4H-pyrrolo[3,4-d][1,3]oxazol-2-yl-(3-hydroxy-5,7-dihydro-4H-[1,2]oxazolo[5,4-c]pyridin-6-ylmethanone; hydrochloride by the appropriate amine and 2-cyclopropyl-6-(oxan-4-ylmethoxy)pyridine-4-carboxylic acid by the appropriate carboxylic acid.

| Ex. | Systematic Name | Amine/Carboxylic acid | MS, m/e |
| --- | --- | --- | --- |
| 3.01 | 1-[5-[2-cyclopropyl-6-(oxan-4-ylmethoxy)pyridine-4-carbonyl]-4,6-dihydropyrrolo[3,4-d][1,3]thiazole-2-carbonyl]piperidine-4-sulfonamide | 1-(5,6-dihydro-4H-pyrrolo[3,4-d][1,3]thiazole-2-carbonyl)piperidine-4-sulfonamide; hydrochloride (intermediate 1.4)/2-cyclopropyl-6-(oxan-4-ylmethoxy)pyridine-4-carboxylic acid (CAS-RN 1810776-23-8) | 576.2 (M + H)$^+$ |
| 3.02 | 1-[5-[2-cyclopropyl-6-(oxan-4-ylmethoxy)pyridine-4-carbonyl]-4,6-dihydrothieno[2,3-c]pyrrole-2-carbonyl]piperidine-4-sulfonamide | 1-(5,6-dihydro-4H-thieno[2,3-c]pyrrole-2-carbonyl)piperidine-4-sulfonamide; hydrochloride (intermediate 1.5)/2-cyclopropyl-6-(oxan-4-ylmethoxy)pyridine-4-carboxylic acid (CAS-RN 1810776-23-8) | 575.3 (M + H)$^+$ |

Example 4

[3-(2,2-Dimethylpropanoylamino)-5-(trifluoromethyl)pyridin-2-yl]methyl 2-(1,4,6,7-tetrahydrotriazolo[4,5-c]pyridine-5-carbonyl)-4,6-dihydropyrrolo[3,4-d][1,3]oxazole-5-carboxylate

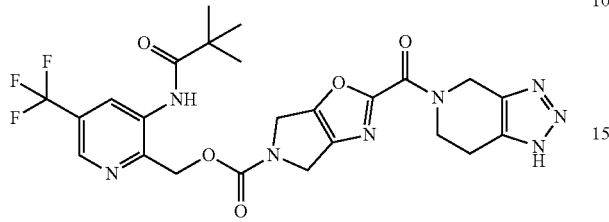

To a solution of N-[2-(hydroxymethyl)-5-(trifluoromethyl)pyridin-3-yl]-2,2-dimethylpropanamide (intermediate 5; 92.2 mg 334 µmol) in acetonitrile (10 mL) was added 1,1'-carbonyldiimidazole (54.1 mg 334 µmol). The reaction mixture was heated to 50° C. for 3 hours. Triethylamine (153 mg 1.52 mmol) and 5,6-dihydro-4H-pyrrolo[3,4-d][1,3]oxazol-2-yl(1,4,6,7-tetrahydrotriazolo[4,5-c]pyridin-5-yl)methanone; hydrochloride (intermediate 4.1; 90 mg 334 µmol) were added and the reaction mixture was heated to reflux. Then after 15 h the reaction mixture was partitioned between sat. aq. ammonium chloride solution and ethyl acetate. The organic layer was washed with brine, dried over magnesium sulfate, filtered and evaporated. Chromatography (silica gel, ethyl acetate/heptane 7:3) produced the title compound (121 mg, 71%). Light yellow foam, MS: 561.4 (M−H)⁻.

The following example was prepared according to example 4, replacing N-[2-(hydroxymethyl)-5-(trifluoromethyppyridin-3-yl]-2,2-dimethylpropanamide (intermediate 5) by the appropriate alcohol and 5,6-dihydro-4H-pyrrolo[3,4-d][1,3]oxazol-2-yl(1,4,6,7-tetrahydrotriazolo[4,5-c]pyridin-5-yl)methanone; hydrochloride (intermediate 4.1) by the appropriate amine.

Example 4.02

[3-(2,2-Dimethylpropanoylamino)-5-(trifluoromethyl)pyridin-2-yl]methyl 2-(4-sulfamoylpiperidine-1-carbonyl)-4,6-dihydrothieno[2,3-c]pyrrole-5-carboxylate and 2,2-dimethyl-N-[2-[[2-(4-sulfamoylpiperidine-1-carbonyl)-4,6-dihydrothieno[2,3-c]pyrrol-5-yl]methyl]-5-(trifluoromethyl)pyridin-3-yl]propanamide

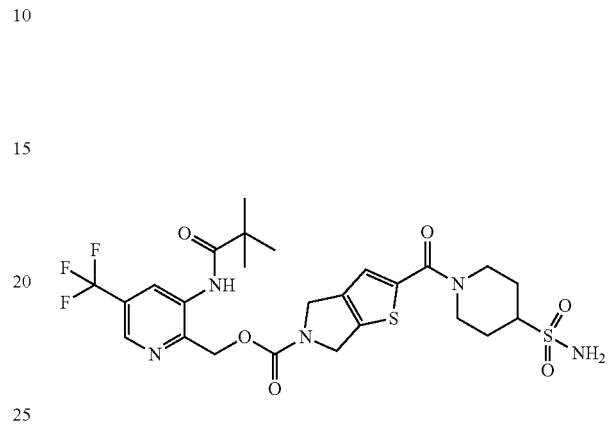

To a solution of N-[2-(hydroxymethyl)-5-(trifluoromethyl)pyridin-3-yl]-2,2-dimethylpropanamide (intermediate 5; 60.5 mg 219 µmol) in acetonitrile (8 ml) was added 1,1'-carbonyldiimidazole (35.5 mg, 219 µmol). The reaction mixture was heated to 50° C. for 3 hours. Triethylamine (121 mg, 1.19 mmol) and 1-(5,6-dihydro-4H-thieno[2,3-c]pyrrole-2-carbonyl)piperidine-4-sulfonamide; hydrochloride (intermediate 1.5; 70 mg 199 µmol) were added and the reaction mixture was heated to reflux. Then after 15 h the reaction mixture was partitioned between sat. aq. ammonium chloride solution and ethyl acetate. The organic layer was washed with brine, dried over magnesium sulfate, filtered and evaporated. Chromatography (Gemini NX 3u 50×4.6 mm) produced the title compound (47 mg, 38%). White foam, MS: 618.3 (M+H)⁺.

| Ex. | Systematic Name | Alcohol/Amine | MS, m/e |
|---|---|---|---|
| 4.01 | [5-chloro-4-cyano-2-(2,2-dimethylpropanoylamino)phenyl]methyl 2-(3-hydroxy-5,7-dihydro-4H-[1,2]oxazolo[5,4-c]pyridine-6-carbonyl)-4,6-dihydropyrrolo[3,4-d][1,3]oxazole-5-carboxylate | N-[4-chloro-5-cyano-2-(hydroxymethyl)phenyl]-2,2-dimethylpropanamide (intermediate 6)/5,6-dihydro-4H-pyrrolo[3,4-d][1,3]oxazol-2-yl-(3-hydroxy-5,7-dihydro-4H-[1,2]oxazolo[5,4-c]pyridin-6-yl)methanone; hydrochloride (intermediate 4) | 569.2 (M + H)⁺ |

Intermediate 1

1,2,3,4-Tetrahydroisoquinolin-6-yl(1,4,6,7-tetrahydrotriazolo[4,5-c]pyridin-5-yl)methanone; hydrochloride

Step 1: tert-Butyl 6-(1,4,6,7-tetrahydrotriazolo[4,5-c]pyridine-5-carbonyl)-3,4-dihydro-1H-isoquinoline-2-carboxylate To a solution of 2-[(2-methylpropan-2-yl)oxycarbonyl]-3,4-dihydro-1H-isoquinoline-6-carboxylic acid (CAS-RN 170097-67-3; 300 mg, 1.08 mmol) in N,N-dimethylformamide (5 ml) was added 4-methylmorpholine (547 mg, 5.41 mmol), 4,5,6,7-tetrahydro-1H-[1,2,3]triazolo[4,5-c]pyridine (CAS-RN 706757-05-3; 141 mg, 1.08 mmol) and O-(7-azabenzotriazol-1-yl)-N,N,N',N'-tetramethyluronium hexafluoro-phosphate (411 mg, 1.08 mmol) at room temperature, then after 18 h the reaction mixture was partitioned between sat. aq. sodium hydrogen carbonate solution and a mixture of ethyl acetate and 2-methyltetrahydrofuran. The organic layer was washed with ammonium chloride solution and brine, dried over magnesium sulfate, filtered and evaporated. Chromatography (silica gel, gradient dichloromethane to dichloromethane/methanol/25% aq. ammonia solution 90:10:2.5) produced the title compound (278 mg, 67%). White foam, MS: 384.3 (M+H)$^+$.

Step 2: 1,2,3,4-Tetrahydroisoquinolin-6-yl(1,4,6,7-tetrahydrotriazolo[4,5-c]pyridin-5-yl)methanone; hydrochloride To a solution of tert-butyl 6-(1,4,6,7-tetrahydrotriazolo[4,5-c]pyridine-5-carbonyl)-3,4-dihydro-1H-isoquinoline-2-carboxylate (263 mg, 686 µmol) in 2-propanol (3 ml) was added hydrogen chloride solution (5-6 M in 2-propanol, 3.84 ml). The reaction mixture was stirred at room temperature for 2 h. The solvent was totally evaporated to produce the title compound (219 mg, 100%). White solid, LC/MS: 284.1 (M+H)$^+$.

The following intermediates were prepared according to intermediate 1, replacing 2-[(2-methylpropan-2-yl)oxycarbonyl]-3,4-dihydro-1H-isoquinoline-6-carboxylic acid by the appropiate carboxylic acid and 4,5,6,7-tetrahydro-1H-[1,2,3]triazolo[4,5-c]pyridine by the appropiate amine

Intermediate 2

2-[2-Cyclopropyl-6-(oxan-4-ylmethoxy)pyridine-4-carbonyl]-1,3-dihydroisoindole-5-carboxylic acid

Step 1: Methyl 2-[2-cyclopropyl-6-(oxan-4-ylmethoxy)pyridine-4-carbonyl]-1,3-dihydroisoindole-5-carboxylate To a solution of methyl 2,3-dihydro-1H-isoindole-5-carboxylate; hydrochloride (CAS-RN 127168-93-8; 400 mg, 1.78 mmol) in N,N-dimethylformamide (6 ml) was added 4-methylmorpholine (1.08 g, 10.7 mmol), 2-cyclopropyl-6-(oxan-4-ylmethoxy)pyridine-4-carboxylic acid (CAS-RN 1810776-23-8; 493 mg, 1.78 mmol) and O-(7-azabenzotriazol-1-yl)-N,N,N',N'-tetramethyluronium hexafluoro-phosphate (676 mg, 1.78 mmol) at room temperature, then after 18 h the reaction mixture was partitioned between sat. aq. sodium hydrogen carbonate solution and a mixture of ethyl acetate and 2-methyltetrahydrofuran. The organic layer was washed with ammonium chloride solution and brine, dried over magnesium sulfate, filtered and evaporated. Chromatography (silica gel, gradient dichloromethane to dichloromethane/methanol/25% aq. ammonia solution 90:10:2.5) produced the title compound (770 mg, 89%). Yellow oil, MS: 437.2 (M+H)$^+$.

Step 2: 2-[2-Cyclopropyl-6-(oxan-4-ylmethoxy)pyridine-4-carbonyl]-1,3-dihydroisoindole-5-carboxylic acid To a solution of methyl 2-[2-cyclopropyl-6-(oxan-4-ylmethoxy)pyridine-4-carbonyl]-1,3-dihydroisoindole-5-carboxylate (742 mg, 1.7 mmol) in tetrahydrofuran and methanol was added Lithium hydroxide solution (2 M in water, 5.1 ml, 10.2 mmol). The reaction mixture was stirred at room temperature for 3 h. The reaction mixture was partitioned between water and diethyl ether. The aqueous layer was acidified with hydrogen chloride solution (1 M in water) and extracted with ethyl acetate. The organic layer was washed with brine, dried over magnesium sulfate, filtered and evaporated to produce the title compound (663 mg, 92%). Off white foam, MS: 423.2 (M+H)$^+$.

| No. | Systematic Name | Carboxylic acid/Amine | MS, m/e |
|---|---|---|---|
| 1.1 | 5,6-dihydro-4H-pyrrolo[3,4-d][1,3]oxazol-2-yl(1,4,6,7-tetrahydrotriazolo[4,5-c]pyridin-5-yl)methanone; hydrochloride | 5-[(2-methylpropan-2-yl)oxycarbonyl]-4,6-dihydropyrrolo[3,4-d][1,3]oxazole-2-carboxylic acid (CAS-RN 1211529-82-6)/ 4,5,6,7-tetrahydro-1H-[1,2,3]triazolo[4,5-c]pyridine (CAS-RN 706757-05-3) | 261.1 (M + H)$^+$ |
| 1.2 | 2,3-dihydro-1H-isoindol-5-yl(1,4,6,7-tetrahydrotriazolo[4,5-c]pyridin-5-yl)methanone; hydrochloride | 2-[(2-methylpropan-2-yl)oxycarbonyl]-1,3-dihydroisoindole-5-carboxylic acid (CAS-RN 149353-71-9)/4,5,6,7-tetrahydro-1H-[1,2,3]triazolo[4,5-c]pyridine (CAS-RN 706757-05-3) | 270.2 (M + H)$^+$ |
| 1.3 | 4,5,6,7-tetrahydro-[1,3]thiazolo[5,4-c]pyridin-2-yl(1,4,6,7-tetrahydrotriazolo[4,5-c]pyridin-5-yl)methanone; hydrochloride | 5-[(2-methylpropan-2-yl)oxycarbonyl]-6,7-dihydro-4H-[1,3]thiazolo[5,4-c]pyridine-2-carboxylic acid (CAS-RN 165948-21-0)/ 4,5,6,7-tetrahydro-1H-[1,2,3]triazolo[4,5-c]pyridine (CAS-RN 706757-05-3) | 291.1 (M + H)$^+$ |
| 1.4 | 1-(5,6-dihydro-4H-pyrrolo[3,4-d][1,3]thiazole-2-carbonyl)piperidine-4-sulfonamide; hydrochloride | 5-[(2-methylpropan-2-yl)oxycarbonyl]-4,6-dihydropyrrolo[3,4-d][1,3]thiazole-2-carboxylic acid (CAS-RN 774533-81-2)/ piperidine-4-sulfonamide hydrochloride | 317.1 (M + H)$^+$ |
| 1.5 | 1-(5,6-dihydro-4H-thieno[2,3-c]pyrrole-2-carbonyl)piperidine-4-sulfonamide; hydrochloride | 5-[(2-methylpropan-2-yl)oxycarbonyl]-4,6-dihydrothieno[2,3-c]pyrrole-2-carboxylic acid (CAS-RN 1369351-45-0)/piperidine-4-sulfonamide hydrochloride | 316.1 (M + H)$^+$ |

Intermediate 3

2-[[3-(2,2-Dimethylpropanoylamino)-5-(trifluoromethyl)pyridin-2-yl]methoxycarbonyl]-1,3-dihydroisoindole-5-carboxylic acid Step 1: 2-O-[[3-(2,2-Dimethylpropanoylamino)-5-(trifluoromethyl)pyridin-2-yl]methyl] 5-O-methyl 1,3-dihydroisoindole-2,5-dicarboxylate To a solution of methyl 2,3-dihydro-1H-isoindole-5-carboxylate; hydrochloride (CAS-RN 127168-93-8; 200 mg, 889 μmop and triethylamine (180 mg, 1.78 mmol) in dichloromethane (4 ml) was added 1,1'-carbonyldiimidazole. After 1 h at room remperature the reaction mixture was partitioned between water and dichloromethane. The organic layer was washed with citric acid solution (0.25 M in water), water and brine, dried over magnesium sulfate, filtered and evaporated. The solid was suspended in tetrahydrofuran (4 ml) and a solution of N-[2-(hydroxymethyl)-5-(trifluoromethyl)pyridin-3-yl]-2,2-dimethylpropanamide (intermediate 5, 246 mg, 889 μmol) in tetrahydrofuran (4 ml) and potassium tert-butoxide solution (2 M in 2-methyltetrahydrofuran; 889 μmol) were added. Then after 30 min. the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:2.5) produced the title compound (364 mg, 85%). Light yellow foam, MS: 480.2 (M+H)$^+$.

Step 2: 2-[[3-(2,2-Dimethylpropanoylamino)-5-(trifluoromethyl)pyridin-2-yl]methoxycarbonyl]-1,3-dihydroisoindole-5-carboxylic acid The title compound was produced in analogy to intermediate 2, step 2, replacing 2-[2-cyclopropyl-6-(oxan-4-ylmethoxy)pyridine-4-carbonyl]-1,3-dihydroisoindole-5-carboxylate by 2-O-[[3-(2,2-dimethylpropanoylamino)-5-(trifluoromethyl)pyridin-2-yl]methyl]5-O-methyl 1,3-dihydroisoindole-2,5-dicarboxylate. Light yellow foam, MS: 464.3 (M+H)$^+$.

Intermediate 3.1

5-[[3-(2,2-Dimethylpropanoylamino)-5-(trifluoromethyl)pyridin-2-yl]methoxycarbonyl]-4,6-dihydropyrrolo[3,4-d][1,3]oxazole-2-carboxylic acid The title compound was produced in analogy to intermediate 3, replacing 2,3-dihydro-1H-isoindole-5-carboxylate; hydrochloride by ethyl 5,6-dihydro-4H-pyrrolo[3,4-d][1,3]oxazole-2-carboxylate; hydrochloride. Light yellow foam. MS: 457.1 (M+H)$^+$.

Intermediate 4

5,6-Dihydro-4H-pyrrolo[3,4-d][1,3]oxazol-2-yl-(3-hydroxy-5,7-dihydro-4H-[1,2]oxazolo[5,4-c]pyridin-6-yl)methanone; hydrochloride Step 1: tert-Butyl 2-(3-hydroxy-5,7-dihydro-4H-[1,2]oxazolo[5,4-c]pyridine-6-carbonyl)-4,6-dihydropyrrolo[3,4-d][1,3]oxazole-5-carboxylate To a suspension of 5-[(2-methylpropan-2-yl)oxycarbonyl]-4,6-dihydropyrrolo[3,4-d][1,3]oxazole-2-carboxylic acid (CAS-RN 1211529-86-6; 308 mg, 1.21 mmol) in dichloromethane (5 ml) was added oxalyl chloride (235 mg, 1.82 mmol) and a catalytic amount of N,N-dimethylformamide at 0° C. After 1 h at room temperature the mixture was diluted with dichloromethane (5 ml) and added to a mixture of 4,5,6,7-tetrahydro-[1,2]oxazolo[5,4-c]pyridin-3-ol; hydrochloride (CAS-RN 64603-91-4; 214 mg, 1.21 mmol) and N,N-diisopropylethylamine (1.57 g, 12.1 mmol) in N,N-dimethylformamide at 0° C. Then after 15 h the reaction mixture was partitioned between sat. aq. ammonium chloride solution and dichloromethane. The organic layer was washed with brine, dried over magnesium sulfate, filtered and evaporated. Chromatography (silica gel, gradient dichloromethane to dichloromethane/methanol 9:1) produced the title compound (239 mg, 52%). Light yellow foam, MS: 377.1 (M+H)$^+$.

Step 2: 5,6-Dihydro-4H-pyrrolo[3,4-d][1,3]oxazol-2-yl-(3-hydroxy-5,7-dihydro-4H-[1,2]oxazolo[5,4-c]pyridin-6-yl)methanone; hydrochloride The title compound was produced in analogy to intermediate 1, step 2, replacing tert-butyl 6-(1,4,6,7-tetrahydrotriazolo[4,5-c]pyridine-5-carbonyl)-3,4-dihydro-1H-isoquinoline-2-carboxylate by tert-butyl 2-(3-hydroxy-5,7-dihydro-4H-[1,2]oxazolo[5,4-c]pyridine-6-carbonyl)-4,6-dihydropyrrolo[3,4-d][1,3]oxazole-5-carboxylate. Light brown foam, MS: 277.1 (M+H)$^+$.

Intermediate 4.1

5,6-Dihydro-4H-pyrrolo[3,4-d][1,3]oxazol-2-yl(1,4,6,7-tetrahydrotriazolo[4,5-c]pyridin-5-yl)methanone; hydrochloride The title compound was produced in anlogy to intermediate 4, replacing 4,5,6,7-tetrahydro-[1,2]oxazolo[5,4-c]pyridin-3-ol; hydrochloride (CAS-RN 64603-91-4) by 4,5,6,7-tetrahydro-1H-[1,2,3]triazolo[4,5-c]pyridine. Light yellow foam, MS: 361.2.

Intermediate 5

N-[2-(Hydroxymethyl)-5-(trifluoromethyl)pyridin-3-yl]-2,2-dimethylpropanamide

Step 1: Methyl 3-pivalamido-5-(trifluoromethyl)picolinate

To a brown solution of methyl 3-amino-5-(trifluoromethyl)picolinate (CAS-RN 866775-17-9; 2.00 g, 8.63 mmol) in pyridine (25 mL) was added pivaloyl chloride (2.08 g, 17.3 mmol) at 0° C. After 20 min the ice-bath was removed, then after 5 h the reaction mixture was partitioned between 1 M aq. hydrochloric acid solution and ethyl acetate. The organic layer was washed with water and brine, dried over magnesium sulfate, filtered and evaporated. Chromatography (silica gel; heptante-ethyl acetate gradient) afforded the title compound (2.46 g, 92%). Light yellow solid, MS: 305.1 (M+H)$^+$.

Step 2: N-(2-(Hydroxymethyl)-5-(trifluoromethyl) pyridin-3-yl)pivalamide

To a clear light yellow solution of methyl 3-pivalamido-5-(trifluoromethyl)picolinate (2.45 g, 8.05 mmol) in tetrahydrofuran (60 mL) was added a solution of calcium chloride (1.79 g, 16.1 mmol) in ethanol (60 mL), then sodium borohydride (914 mg, 24.2 mmol) was added in 3 portions over a period of 30 min. The white suspension was stirred for 90 min at room temperature, then partitioned between water and sat. aq. ammonium chloride solution. The organic layer was washed with brine, dried over magnesium sulfate, filtered, and evaporated. Chromatography (silica gel; heptane-ethyl acetate gradient) afforded the title compound (1.97 g; 89%). Light yellow viscous oil, MS: 277.1 (M+H)$^+$.

Intermediate 6

N-[4-Chloro-5-cyano-2-(hydroxymethyl)phenyl]-2,2-dimethylpropanamide

Step 1: Methyl 4-bromo-5-chloro-2-pivalamidobenzoate

The title compound was produced in analogy to intermediate 5, step 1 from methyl 2-amino-4-bromo-5-chlorobenzoate (CAS-RN 1445322-56-4). White solid. MS: 350.0 (M+H)$^+$.

Step 2: Methyl 5-chloro-4-cyano-2-pivalamidobenzoate

A mixture of methyl 4-bromo-5-chloro-2-pivalamidobenzoate (3.14 g, 9.01 mmol), tris(dibenzylideneacetone)dipalladium(0) (82.5 mg, 90.1 µmol), 1,1'-bis(diphenylphosphino)ferrocene (150 mg, 270 µmol), and zinc cyanide (582 mg, 4.95 mmol), zinc powder (23.6 mg, 360 µmol) and zinc acetate (66.1 mg, 360 µmol) in N,N-dimethylformamide (48 mL) and water (1.5 mL) was heated for 20 min at 130° C. under microwave irradiation. After removal of insoluble material under vacuum and concentration of the filtrate, the residue was partitioned between 50% aq. sodium hydrogencarbonate solution and ethyl acetate. The organic layer was washed water and brine, dried over magnesium sulfate, filtered and evaporated. Chromatography (silica gel; heptane-dichloromethane gradient) produced the title compound (2.00 g, 75%). Light yellow solid. MS: 295.1 (M+H)$^+$.

Step 3: N-(4-Chloro-5-cyano-2-(hydroxymethyl)phenyl)pivalamide

The title compound was produced in analogy to intermediate 5, step 2 from methyl 5-chloro-4-cyano-2-pivalamidobenzoate. Light yellow solid. MS: 267.1 (M+H)$^+$.

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

What is claimed is:
1. A compound of formula (II):

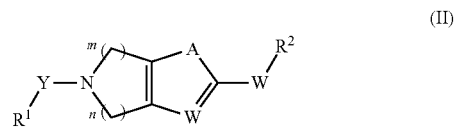

wherein:
R$^1$ is selected from the group consisting of:
  i) phenyl substituted by R$^3$, R$^4$ and R$^5$,
  ii) phenyl-C$_{1-6}$-alkyl substituted by R$^3$, R$^4$ and R$^5$,
  iii) phenoxy-C$_{1-6}$-alkyl substituted by R$^3$, R$^4$ and R$^5$,
  iv) phenyl-C$_{2-6}$-alkenyl substituted by R$^3$, R$^4$ and R$^5$,
  v) phenyl-C$_{2-6}$-alkynyl substituted by R$^3$, R$^4$ and R$^5$,
  vi) pyridinyl substituted by R$^3$, R$^4$ and R$^5$,
  vii) pyridinyl-C$_{1-6}$-alkyl substituted by R$^3$, R$^4$ and R$^5$,
  viii) pyridinyl-C$_{2-6}$-alkenyl substituted by R$^3$, R$^4$ and R$^5$,
  ix) pyridinyl-C$_{2-6}$-alkynyl substituted by R$^3$, R$^4$ and R$^5$,
  x) thiophenyl substituted by R$^3$, R$^4$ and R$^5$,
  xi) thiophenyl-C$_{1-6}$-alkyl substituted by R$^3$, R$^4$ and R$^5$,
  xii) thiophenyl-C$_{2-6}$-alkenyl substituted by R$^3$, R$^4$ and R$^5$, and
  xiii) thiophenyl-C$_{2-6}$-alkynyl substituted by R$^3$, R$^4$ and R$^5$;
Y is selected from the group consisting of:
  x) C$_{3-8}$-cycloalkyl-C$_{1-6}$-alkyl,
  xi) C$_{3-8}$-cycloalkyl-C$_{1-6}$-alkoxy,
  xii) C$_{3-8}$-cycloalkoxy,
  xiii) C$_{3-8}$-cycloalkoxy-C$_{1-6}$-alkyl,
  xiv) C$_{1-6}$-alkylamino,
  xv) C$_{1-6}$-alkylcarbonylamino,
  xvi) C$_{3-8}$-cycloalkylcarbonylamino,
  xvii) C$_{1-6}$-alkyltetrazolyl,
  xviii) C$_{1-6}$-alkyltetrazolyl-C$_{1-6}$-alkyl, and
  xix) heterocycloalkyl-C$_{1-6}$-alkoxy;
R$^4$ and R$^5$ are independently selected from the group consisting of:
  i) H,
  ii) halogen,
  iii) hydroxy,
  iv) cyano,
  v) C$_{1-6}$-alkyl,
  vi) C$_{1-6}$-alkoxy,
  vii) C$_{1-6}$-alkoxy-C$_{1-6}$-alkyl,
  viii) halo-C$_{1-6}$-alkoxy,
  ix) halo-C$_{1-6}$-alkyl,
  x) hydroxy-C$_{1-6}$-alkyl,
  xi) C$_{3-8}$-cycloalkyl,
  xii) C$_{3-8}$-cycloalkyl-C$_{1-6}$-alkyl,
  xiii) C$_{3-8}$-cycloalkyl-C$_{1-6}$-alkoxy,
  xiv) C$_{3-8}$-cycloalkoxy,
  xv) C$_{3-8}$-cycloalkoxy-C$_{1-6}$-alkyl,
  xvi) C$_{1-6}$-alkylcarbonylamino, xvii) $C_{3-8}$-cycloalkylcarbonylamino,
xviii) $C_{1-6}$-alkyltetrazolyl,
xix) $C_{1-6}$-alkyltetrazolyl-$C_{1-6}$-alkyl, and
xx) heterocycloalkyl-$C_{1-6}$-alkoxy;

$R^6$ is selected from the group consisting of:
  i) H,
  ii) $C_{1-6}$-alkyl, and
  i) —OC(O)—, and
  ii) —C(O)—;

A is selected from the group consisting of:
  i) —O—, and
  ii) —S—;

X is selected from the group consisting of:
  i) —N—, and
  ii) —CH—;

W is selected from the group consisting of:
  i) —C(O)—, and
  ii) —S(O)$_2$—;

$R^2$ is selected from the ring systems O, AO, AW, AX, AY and AZ;

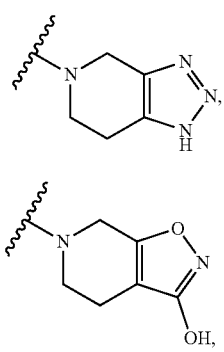

O

AO

AW

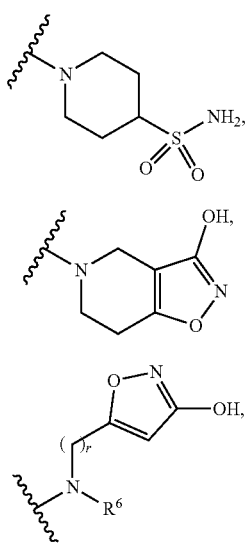

AX

AY

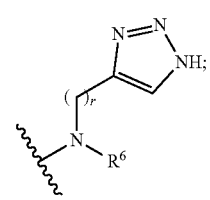

AZ $R^3$ is selected from the group consisting of:
  i) halogen,
  ii) hydroxy,
  iii) cyano, $C_{1-6}$-alkyl,
  iv) $C_{1-6}$-alkoxy,
  v) $C_{1-6}$-alkoxy-$C_{1-6}$-alkyl,
  vi) halo-$C_{1-6}$-alkoxy,
  vii) halo-$C_{1-6}$-alkyl,
  viii) hydroxy-$C_{1-6}$-alkyl,
  ix) $C_{3-8}$-cycloalkyl,
  iii) $C_{3-8}$-cycloalkyl;

m is 1;
n is 1 or 2; and
r is 1, 2 or 3;

or a pharmaceutically acceptable salt thereof.

2. A compound according to claim 1, wherein:
$R^1$ is selected from the group consisting of:
  i) phenyl-$C_{1-6}$-alkyl substituted by $R^3$, $R^4$ and $R^5$,
  ii) pyridinyl substituted by $R^3$, $R^4$ and $R^5$, and
  iii) pyridinyl-$C_{1-6}$-alkyl substituted by $R^3$, $R^4$ and $R^5$;

Y is selected from the group consisting of:
  i) —OC(O)—, and
  ii) —C(O)—;

A is selected from the group consisting of:
  i) —O—, and
  ii) —S—;

X is selected from the group consisting of:
  i) —N—, and
  ii) —CH—;

W is —C(O)—;

$R^2$ is selected from the ring systems O, AO and AW;

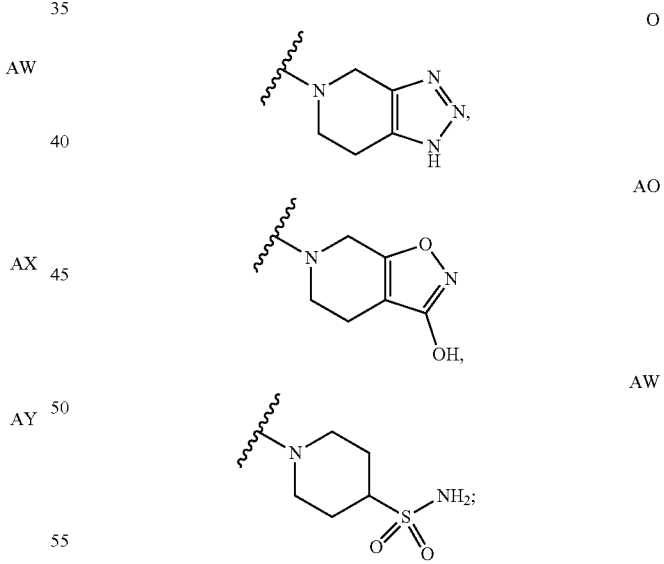

O

AO

AW $R^3$ is selected from the group consisting of:
  i) $C_{1-6}$-alkylcarbonylamino, and
  ii) tetrahydropyranyl-$C_{1-6}$-alkoxy;

$R^4$ is selected from the group consisting of:
  i) cyano,
  ii) $C_{3-8}$-cycloalkyl, and
  iii) halo-$C_{1-6}$-alkyl;

$R^5$ is selected from the group consisting of:
  i) H, and
  ii) halogen;

m is 1; and n is 1 or 2;

or a pharmaceutically acceptable salt thereof.

3. A compound according to claim 1, or a pharmaceutically acceptable salt thereof, wherein $R^1$ is selected from the group consisting of:
i) phenyl-$C_{1-6}$-alkyl substituted by $R^3$, $R^4$ and $R^5$,
ii) pyridinyl substituted by $R^3$, $R^4$ and $R^5$, and
iii) pyridinyl-$C_{1-6}$-alkyl substituted by $R^3$, $R^4$ and $R^5$.

4. A compound according to claim 1, or a pharmaceutically acceptable salt thereof, wherein $R^1$ is selected from the group consisting of:
i) phenyl-$C_{1-6}$-alkyl substituted by $R^3$, $R^4$ and $R^5$, and
ii) pyridinyl substituted by $R^3$, $R^4$ and $R^5$.

5. A compound according to claim 1, or a pharmaceutically acceptable salt thereof, wherein Y is —OC(O)—.

6. A compound according to claim 1, or a pharmaceutically acceptable salt thereof, wherein A is —S—.

7. A compound according to claim 1, or a pharmaceutically acceptable salt thereof, wherein A is —O—.

8. A compound according to claim 1, or a pharmaceutically acceptable salt thereof, wherein X is —N—.

9. A compound according to claim 1, or a pharmaceutically acceptable salt thereof, wherein W is —C(O)—.

10. A compound according to claim 1, or a pharmaceutically acceptable salt thereof, wherein $R^2$ is O, AO, or AW.

11. A compound according to claim 1, or a pharmaceutically acceptable salt thereof, wherein $R^2$ is O or AO.

12. A compound according to claim 1, or a pharmaceutically acceptable salt thereof, wherein $R^3$ is:
i) $C_{1-6}$-alkylcarbonylamino, or
ii) tetrahydropyranyl-$C_{1-6}$-alkoxy.

13. A compound according to claim 1, or a pharmaceutically acceptable salt thereof, wherein $R^4$ is:
i) cyano,
ii) $C_{3-8}$-cycloalkyl, or
iii) halo-$C_{1-6}$-alkyl.

14. A compound according to claim 1, or a pharmaceutically acceptable salt thereof, wherein $R^4$ is:
i) cyano, or
ii) $C_{3-8}$-cycloalkyl.

15. A compound according to claim 1, or a pharmaceutically acceptable salt thereof, wherein $R^5$ is:
i) H, or
ii) halogen.

16. A compound according to claim 1, or a pharmaceutically acceptable salt thereof, wherein n is 2.

17. A compound according to claim 1, or a pharmaceutically acceptable salt thereof, wherein m and n are both 1.

18. A compound according to claim 1, or a pharmaceutically acceptable salt thereof, wherein:
$R^1$ is selected from the group consisting of:
i) phenyl-$C_{1-6}$-alkyl substituted by $R^3$, $R^4$ and $R^5$, and
ii) pyridinyl substituted by $R^3$, $R^4$ and $R^5$;
Y is selected from the group consisting of:
i) —OC(O)—, and
ii) —C(O)—;
A is —O—;
X is N;
W is —C(O)—;
$R^2$ is selected from the ring systems O and AO;

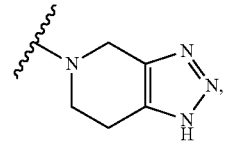

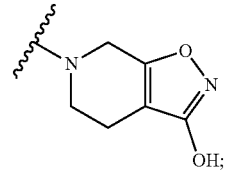

$R^3$ is selected from the group consisting of:
i) $C_{1-6}$-alkylcarbonylamino, and
ii) tetrahydropyranyl-$C_{1-6}$-alkoxy;
$R^4$ is selected from the group consisting of:
i) cyano, and
ii) $C_{3-8}$-cycloalkyl;
$R^5$ is selected from the groups consisting of:
i) H, and
ii) halogen;
m and n are both 1.

19. A compound according to claim 1, wherein the compound is of formula (II),

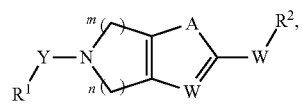

wherein:
$R^1$ is:
i) phenyl-$C_{1-6}$-alkyl substituted by $R^3$, $R^4$ and $R^5$,
ii) pyridinyl substituted by $R^3$, $R^4$ and $R^5$, or
iii) pyridinyl-$C_{1-6}$-alkyl substituted by $R^3$, $R^4$ and $R^5$;
Y is:
i) —OC(O)—, or
ii) —C(O)—;
A is:
i) —O—, or
ii) —S—;
X is:
i) —N—, or
ii) —CH—;
W is —C(O)—;
$R^2$ is selected from the ring systems O, AO and AW;

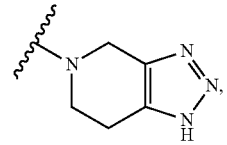

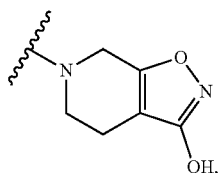
AO

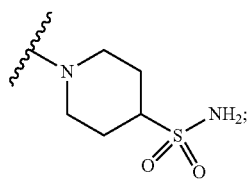
AW

R³ is selected from the group consisting of:
  i) C₁₋₆-alkylcarbonylamino, and
  ii) tetrahydropyranyl-C₁₋₆-alkoxy;
R⁴ is selected from the group consisting of:
  i) cyano,
  ii) C₃₋₈-cycloalkyl, and
  iii) halo-C₁₋₆-alkyl;
R⁵ is selected from the group consisting of:
  i) H, and
  ii) halogen;
m is 1; and
n is selected from 1 and 2;
or a pharmaceutically acceptable salt thereof.

20. A compound according to claim 1, wherein the compound is of formula (II),

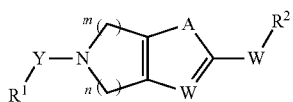

wherein:
R¹ is selected from the group consisting of:
  i) phenyl-C₁₋₆-alkyl substituted by R³, R⁴ and R⁵, and
  ii) pyridinyl substituted by R³, R⁴ and R⁵;
Y is selected from the groups consisting of:
  i) —OC(O)—, and
  ii) —C(O)—;
A is —O—;
X is —N—;
W is —C(O)—;
R² is selected from the ring systems O and AO;

O

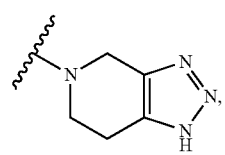

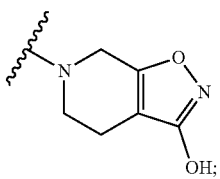
AO

R³ is selected from the group consisting of:
  i) C₁₋₆-alkylcarbonylamino, and
  ii) tetrahydropyranyl-C₁₋₆-alkoxy;
R⁴ is selected from the group consisting of:
  i) cyano, and
  ii) C₃₋₈-cycloalkyl;
R⁵ is selected from the group consisting of:
  i) H, and
  ii) halogen; and
m and n are both 1;
or a pharmaceutically acceptable salt thereof.

21. A compound according to claim 1, wherein the compound is:
[2-cyclopropyl-6-(oxan-4-ylmethoxy)pyridin-4-yl]-[2-(1,4,6,7-tetrahydrotriazolo[4,5-c] pyridine-5-carbonyl)-4,6-dihydropyrrolo[3,4-d][1,3]oxazol-5-yl]methanone;
[2-cyclopropyl-6-(oxan-4-ylmethoxy)pyridin-4-yl]-[2-(1,4,6,7-tetrahydrotriazolo[4,5-c] pyridine-5-carbonyl)-6,7-dihydro-4H-[1,3]thiazolo[5,4-c]pyridin-5-yl]methanone;
[3-(2,2-dimethylpropanoylamino)-5-(trifluoromethyl)pyridin-2-yl]methyl 2-(4-sulfamoylpiperidine-1-carbonyl)-4,6-dihydropyrrolo[3,4-d][1,3]oxazole-5-carboxylate;
[2-cyclopropyl-6-(oxan-4-ylmethoxy)pyridin-4-yl]-[2-(3-hydroxy-5,7-dihydro-4H-[1,2]oxazolo[5,4-c]pridine-6-carbonyl)-4,6-dihydropyrrolo[3,4-d][1,3]oxazol-5-yl]methanone;
1-[5-[2-cyclopropyl-6-(oxan-4-ylmethoxy)pyridine-4-carbonyl]-4,6-dihydropyrrolo[3,4-d][1,3]thiazole-2-carbonyl]piperidine-4-sulfonamide;
1-[5-[2-cyclopropyl-6-(oxan-4-ylmethoxy)pyridine-4-carbonyl]-4,6-dihydrothieno[2,3-c]pyrrole-2-carbonyl]piperidine-4-sulfonamide;
[3-(2,2-dimethylpropanoylamino)-5-(trifluoromethyl)pyridin-2-yl]methyl 2-(1,4,6,7-tetrahydrotriazolo[4,5-c] pyridine-5-carbonyl)-4,6-dihydropyrrolo[3,4-d][1,3]oxazole-5-carboxylate;
[5-chloro-4-cyano-2-(2,2-dimethylpropanoylamino)phenyl]methyl 2-(3-hydroxy-5,7-dihydro-4H-[1,2]oxazolo[5,4-c]pridine-6-carbonyl)-4,6-dihydropyrrolo[3,4-d][1,3]oxazole-5-carboxylate; or
[3-(2,2-dimethylpropanoylamino)-5-(trifluoromethyl)pyridin-2-yl]methyl 2-(4-sulfamoylpiperidine-1-carbonyl)-4,6-dihydrothieno[2,3-c]pyrrole-5-carboxylate;
or a pharmaceutically acceptable salt thereof.

22. A compound according to claim 1, wherein the compound is:
[2-cyclopropyl-6-(oxan-4-ylmethoxy)pyridin-4-yl]-[2-(1,4,6,7-tetrahydrotriazolo[4,5-c] pyridine-5-carbonyl)-4,6-dihydropyrrolo[3,4-d][1,3]oxazol-5-yl]methanone;
[2-cyclopropyl-6-(oxan-4-ylmethoxy)pyridin-4-yl]-[2-(3-hydroxy-5,7-dihydro-4H-[1,2]oxazolo[5,4-c]pridine-6-carbonyl)-4,6-dihydropyrrolo[3,4-d][1,3]oxazol-5-yl]methanone; or
[5-chloro-4-cyano-2-(2,2-dimethylpropanoylamino)phenyl]methyl 2-(3-hydroxy-5,7-dihydro-4H-[1,2]oxazolo

[5,4-c]pridine-6-carbonyl)-4,6-dihydropyrrolo[3,4-d][1,3]oxazole-5-carboxylate;
or a pharmaceutically acceptable salt thereof.

23. A process to prepare a compound according to claim 1, or a pharmaceutically acceptable salt thereof, comprising the reaction of a compound of formula (III) in the presence of a compound of formula (IV), wherein $R^1$, $R^2$, Y, W, A, X, m and n are as defined in claim 1, and wherein when Y is —C(O)—, then G is halogen or hydoxy; and wherein when Y is —OC(O)—, then G is chloro:

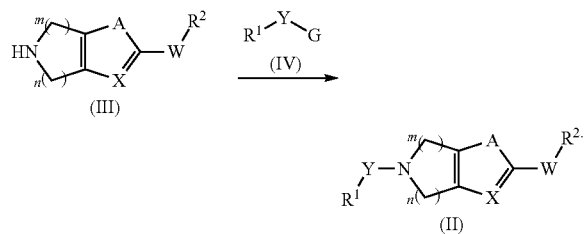

24. A pharmaceutical composition comprising a compound according to claim 1, or a pharmaceutically acceptable salt thereof, and a therapeutic ally inert carrier.

25. A method for the treatment of an ocular condition, comprising administering an effective amount of a compound according to claim 1, or a pharmaceutically acceptable salt thereof, wherein the ocular condition is proliferative retinopathy, non-proliferative (diabetic) retinopathy, dry macular degeneration, wet age-related macular degeneration (AMD), macular edema, central arterial occlusion, central venous occlusion, traumatic injury, or glaucoma.

26. A compound according claim 1, or a pharmaceutically acceptable salt thereof, manufactured by:
reacting a compound of formula (III) in the presence of a compound of formula (IV), wherein $R^1$, $R^2$, Y, W, A, X, m and n are as defined in claim 1, and wherein when Y is —C(O)—, then G is halogen or hydoxy; and wherein when Y is —OC(O)—, then G is chloro:

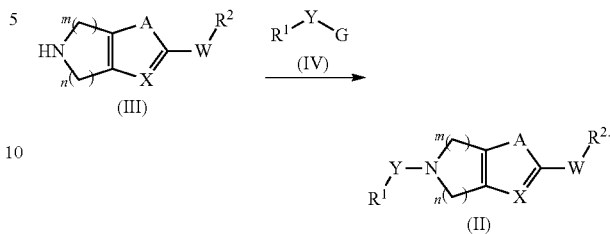

27. A pharmaceutical composition comprising a compound according to claim 21, or a pharmaceutically acceptable salt thereof, and a therapeutically inert carrier.

28. A pharmaceutical composition comprising a compound according to claim 22, or a pharmaceutically acceptable salt thereof, and a therapeutically inert carrier.

29. A method for the treatment of an ocular condition, comprising administering an effective amount of a compound according to claim 21, or a pharmaceutically acceptable salt thereof, wherein the ocular condition is proliferative retinopathy, non-proliferative (diabetic) retinopathy, dry macular degeneration, wet age-related macular degeneration (AMD), macular edema, central arterial occlusion, central venous occlusion, traumatic injury, or glaucoma.

30. A method for the treatment of an ocular condition, comprising administering an effective amount of a compound according to claim 22, or a pharmaceutically acceptable salt thereof, wherein the ocular condition is proliferative retinopathy, non-proliferative (diabetic) retinopathy, dry macular degeneration, wet age-related macular degeneration (AMD), macular edema, central arterial occlusion, central venous occlusion, traumatic injury, or glaucoma.

* * * * *